US012709017B2

(12) United States Patent
Parthiban et al.

(10) Patent No.: US 12,709,017 B2
(45) Date of Patent: Aug. 18, 2026

(54) PHYSICIAN CONSOLE GENERATING HAPTIC VIBRATION FOR TELEOPERATION

(71) Applicant: AURIS HEALTH, INC., Redwood City, CA (US)

(72) Inventors: Chembian Parthiban, Fremont, CA (US); Yanan Huang, Sunnyvale, CA (US); Hossein Taheri, Foster City, CA (US); Henry A Peck, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 9 days.

(21) Appl. No.: 18/895,289

(22) Filed: Sep. 24, 2024

(65) Prior Publication Data

US 2025/0010488 A1 Jan. 9, 2025

Related U.S. Application Data

(63) Continuation of application No. PCT/IB2023/052642, filed on Mar. 17, 2023.

(Continued)

(51) Int. Cl.

*B25J 13/02* (2006.01)
*A61B 1/00* (2006.01)

(Continued)

(52) U.S. Cl.

CPC ............. *B25J 13/025* (2013.01); *A61B 34/35* (2016.02); *A61B 34/76* (2016.02); *B25J 9/1682* (2013.01); *B25J 9/1689* (2013.01)

(58) Field of Classification Search

CPC ...... B25J 13/025; B25J 9/1682; B25J 9/1689; A61B 34/35; A61B 34/76; A61B 1/00055;

(Continued)

(56) References Cited

U.S. PATENT DOCUMENTS 6,810,281 B2 * 10/2004 Brock .................. A61B 5/0086 600/407
8,332,072 B1 12/2012 Schaible et al.

(Continued)

FOREIGN PATENT DOCUMENTS

CN 112043397 B 9/2021
CN 113648066 A 11/2021
EP 3586782 A1 1/2020

OTHER PUBLICATIONS

International Search Report and Written Opinion dated Jun. 26, 2023, for International Application No. PCT/IB2023/052642, 13 pages.

(Continued)

*Primary Examiner* — Harry Y Oh
(74) *Attorney, Agent, or Firm* — FBT Gibbons LLP

(57) ABSTRACT

A medical system may include a first haptic interface device, one or more input sensors, one or more processors, and memory storing instructions. When executed by the one or more processors, the instructions can cause the one or more processors to: receive a first input signal from the one or more input sensors; send to the first haptic interface device a kinesthetic haptic feedback signal based at least on the first input signal for a kinesthetic haptic feedback; receive a second input signal from the one or more input sensors; and send to the first haptic interface device a vibrational tactile feedback signal based at least on the second input signal for a vibrational tactile feedback.

20 Claims, 28 Drawing Sheets

Related U.S. Application Data

(60) Provisional application No. 63/323,934, filed on Mar. 25, 2022.

(51) Int. Cl.

| | |
|---|---|
| ***A61B 34/00*** | (2016.01) |
| ***A61B 34/20*** | (2016.01) |
| ***A61B 34/30*** | (2016.01) |
| ***A61B 34/35*** | (2016.01) |
| ***A61B 34/37*** | (2016.01) |
| ***A61B 90/00*** | (2016.01) |
| ***B25J 9/16*** | (2006.01) |

(58) Field of Classification Search

CPC ... A61B 1/00147; A61B 1/3132; A61B 34/37; A61B 34/74; A61B 2034/2051; A61B 2034/2059; A61B 2034/2061; A61B 2034/302; A61B 2090/306; A61B 2090/309; A61B 2090/376; A61B 2562/0219; A61B 2562/0223; A61B 34/30; A61B 2034/301

See application file for complete search history.

(56) References Cited

U.S. PATENT DOCUMENTS

| | | | | |
|---|---|---|---|---|
| 9,198,714 | B2 | 12/2015 | Worrell et al. | |
| 9,763,741 | B2 | 9/2017 | Alvarez et al. | |
| 10,130,429 | B1 * | 11/2018 | Weir | A61B 34/76 |
| 11,490,981 | B2 | 11/2022 | Denlinger et al. | |
| 2011/0264108 | A1 | 10/2011 | Nowlin et al. | |
| 2014/0005682 | A1 * | 1/2014 | Worrell | A61B 34/77 606/130 |
| 2018/0132953 | A1 * | 5/2018 | Neupert | B25J 13/085 |
| 2020/0289229 | A1 * | 9/2020 | Denlinger | G06T 7/50 |
| 2023/0310108 | A1 * | 10/2023 | Balter | A61B 34/74 606/1 |
| 2023/0372014 | A1 * | 11/2023 | Gao | A61B 34/10 |

OTHER PUBLICATIONS

European Extended Search Report and Written Opinion dated Jan. 30, 2026, for Application No. 23774097.2, 12 pages.

* cited by examiner 154
158
158
152
150
180a
180a
170
174
174
172
156
162

PHYSICIAN CONSOLE GENERATING HAPTIC VIBRATION FOR TELEOPERATION

PRIORITY

This application is a continuation of International Patent Application No. PCT/IB2023/052642, filed Mar. 17, 2023, entitled "Physician Console Generating Haptic Vibration for Teleoperation," which claims priority to U.S. Provisional Patent Application No. 63/323,934, entitled "Physician Console Generating Haptic Vibration for Teleoperation," filed Mar. 25, 2022, the disclosures of each of which are incorporated by reference herein, in their entirety.

TECHNICAL FIELD

This application relates to controllers, and in particular, to controllers for robotically enabled teleoperated systems including medical systems.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically enabled medical system may be used to control the insertion and/or manipulation of the instrument and an end effector thereof. The robotically enabled medical system may include a robotic arm, or other instrument positioning device. The robotically enabled medical system may also include a controller used to control the positioning of the instrument during the procedure.

SUMMARY

In a first aspect, a robotically enabled teleoperated medical system is described. The medical system includes a first haptic interface device, one or more input sensors, one or more processors, and memory storing instructions. When the instructions are executed by the one or more processors, the instruction cause the one or more processors to: receive a first input signal from the one or more input sensors; send to the first haptic interface device a kinesthetic haptic feedback signal based at least on the first input signal for a kinesthetic haptic feedback; receive a second input signal from the one or more input sensors; and send to the first haptic interface device a vibrational tactile feedback signal based at least on the second input signal for a vibrational tactile feedback.

The system may include one or more of the following features, in any combination: (a) a first robotic arm; (b) wherein the first input signal is based on a difference between a master command and a movement of the first robotic arm; (c) a second robotic arm that is distinct from the first robotic arm; (d) wherein the second input signal is derived from a collision between the first robotic arm and the second robotic arm; (e) wherein the second input signal is derived from a criterion that includes a distance between the first robotic arm and the second robotic arm being less than a first distance threshold; (f) wherein the second input signal is derived from a criterion that includes a collision between a first surgical instrument coupled to the first robotic arm and a second surgical instrument coupled to the second robotic arm; (g) wherein the second input signal is derived from a criterion that includes a distance between a first surgical instrument coupled to the first robotic arm and a second surgical instrument coupled to the second robotic arm being less than a second distance threshold; (h) the second input signal is derived from a criterion that includes a detection of a fault in the medical system; (i) the second input signal is derived from a criterion that includes a detection of the first haptic interface device at a predefined boundary; (j) a second haptic interface device that is distinct and separate from the first haptic interface device; (k) wherein the second input signal is derived from a criterion that includes a collision between the first haptic interface device and the second haptic interface device; (l) wherein the second input signal is derived from a criterion that includes a distance between the first haptic interface device and the second haptic interface device being less than a third distance threshold; (m) wherein the kinesthetic haptic feedback includes a continuous force applied against a user input; (n) wherein the second input signal is derived from a criterion that includes a plurality of events; and a distinct haptic feedback signal is selected as the vibrational tactile feedback signal for a respective event of the plurality of events; (o) wherein the vibrational tactile feedback includes a component with a frequency of at least 10 Hz; and/or (p) wherein the first haptic interface device further includes a motor to provide a torque about a roll axis of the first haptic interface device in response to a user input on the first haptic interface device.

In another aspect, provided is a method that involves or includes: receiving a first input signal from one or more input sensors; sending to a first haptic interface device a kinesthetic haptic feedback signal based at least on the first input signal for a kinesthetic haptic feedback; receiving a second input signal from the one or more input sensors; and sending to the first haptic interface device a vibrational tactile feedback signal based at least on the second input signal for a vibrational tactile feedback.

In another aspect, a robotically enabled teleoperated medical system is described. The medical system includes a first haptic interface device, one or more input sensors, one or more processors, and memory storing instructions. When the instructions are executed by the one or more processors, the instruction cause the one or more processors to: receive a first input signal from the one or more input sensors; send to the first haptic interface device a first haptic feedback signal based at least on the first input signal for a first haptic feedback; receive a second input signal from the one or more input sensors; and send to the first haptic interface device a second tactile feedback signal based at least on the second input signal for a second tactile feedback.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
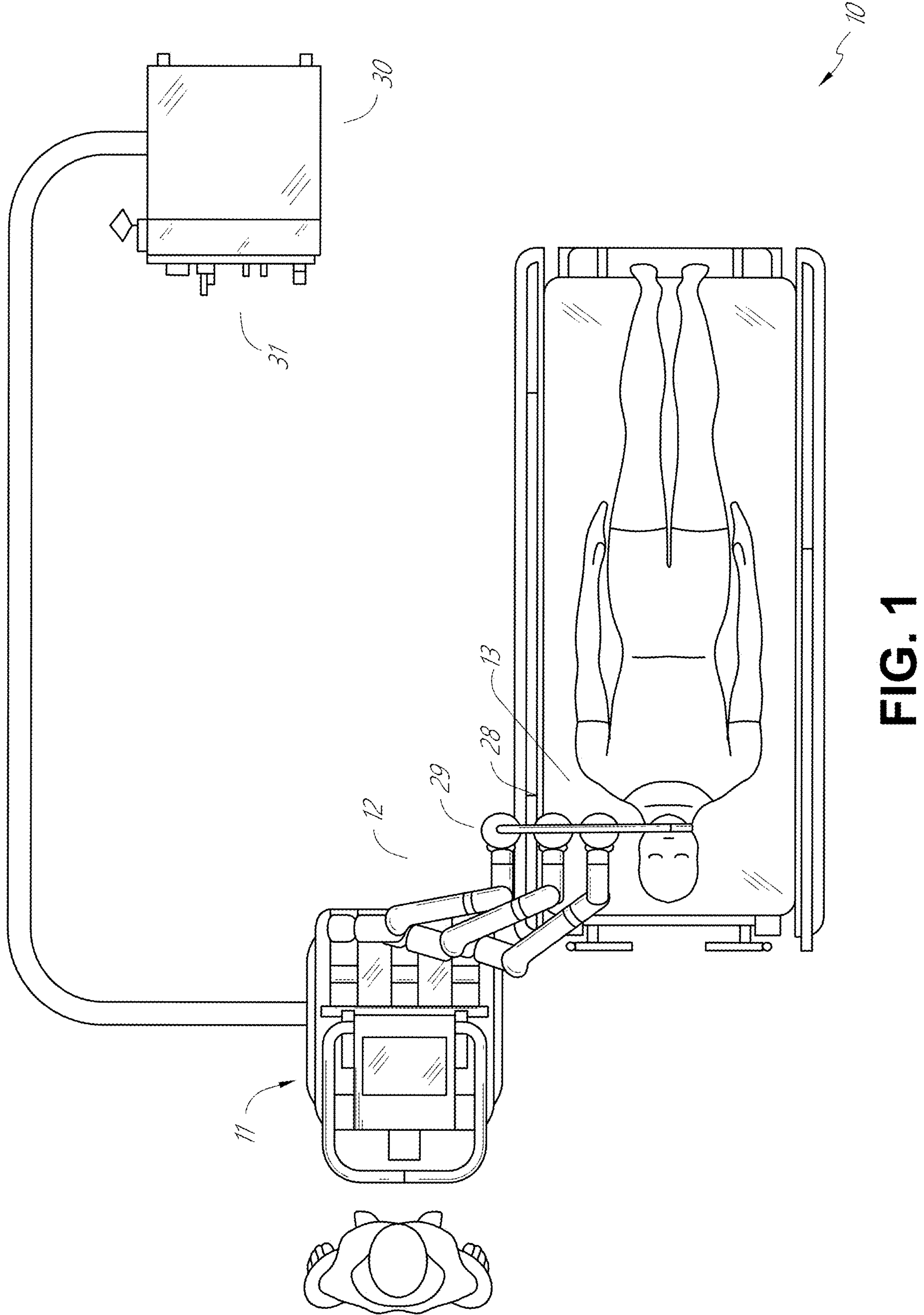
FIG. 1 illustrates an embodiment of a cart-based robotic system arranged for diagnostic and/or therapeutic bronchoscopy procedure(s).
Figure 2:
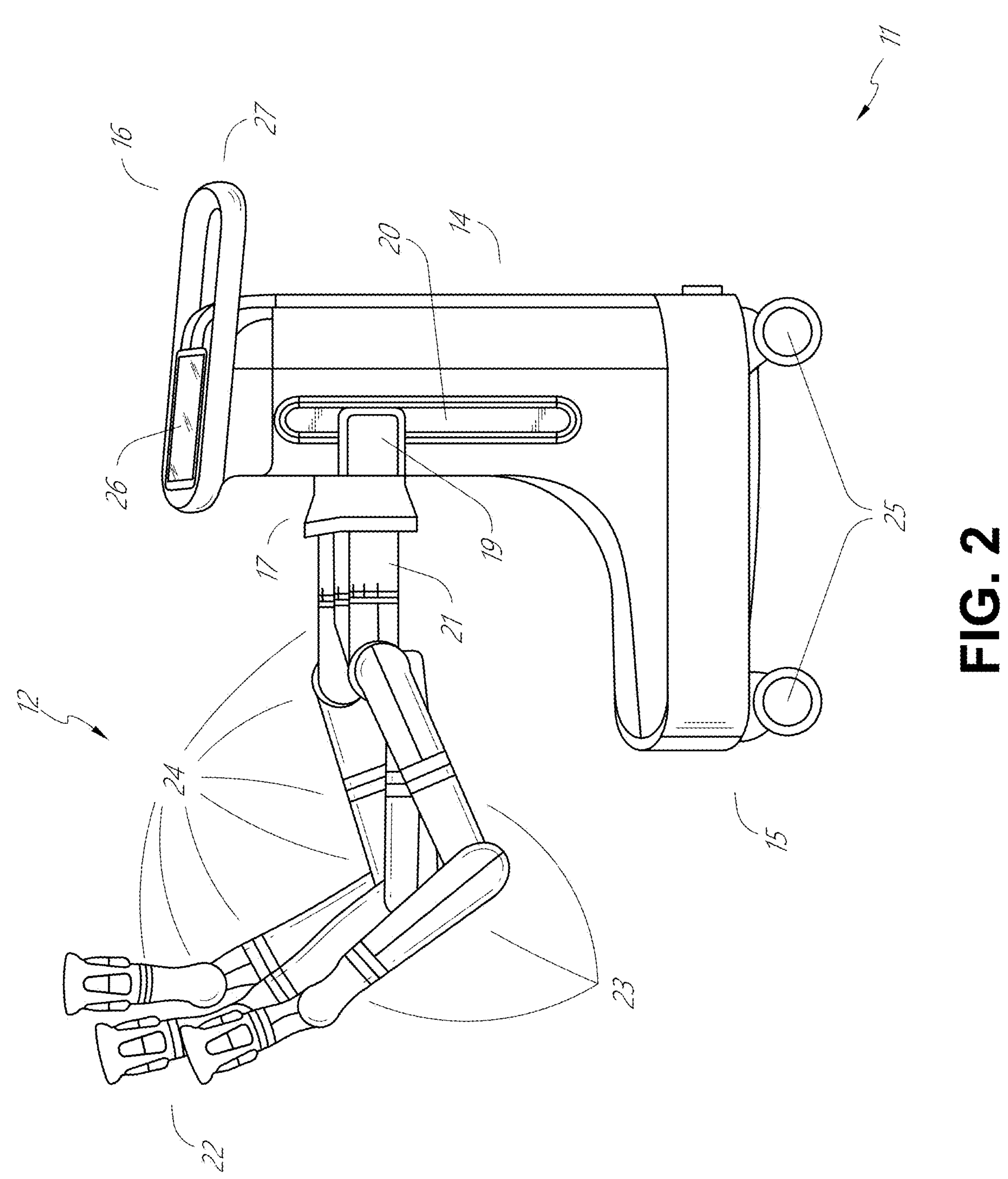
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the robotic system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The robotic system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in robotic system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
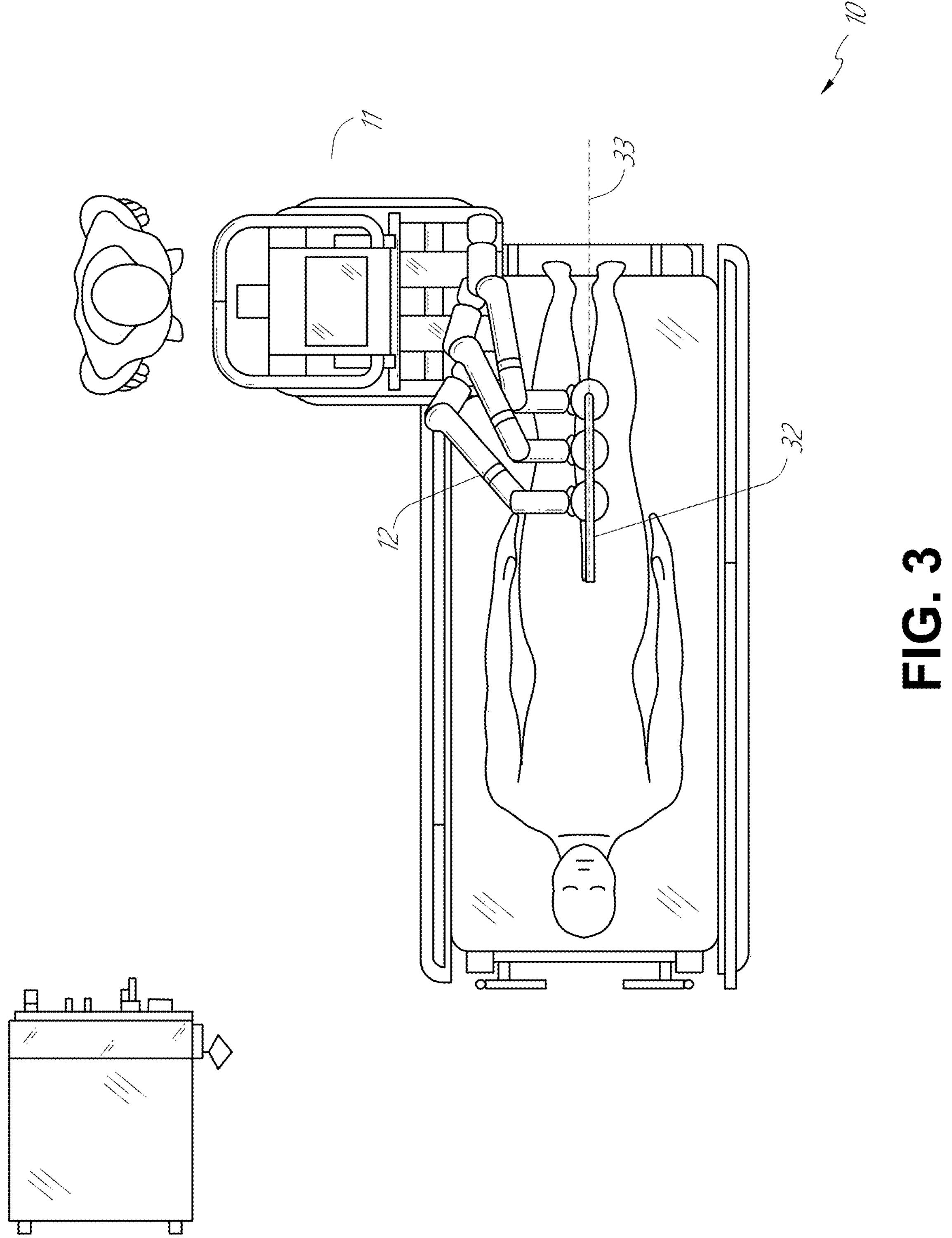
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
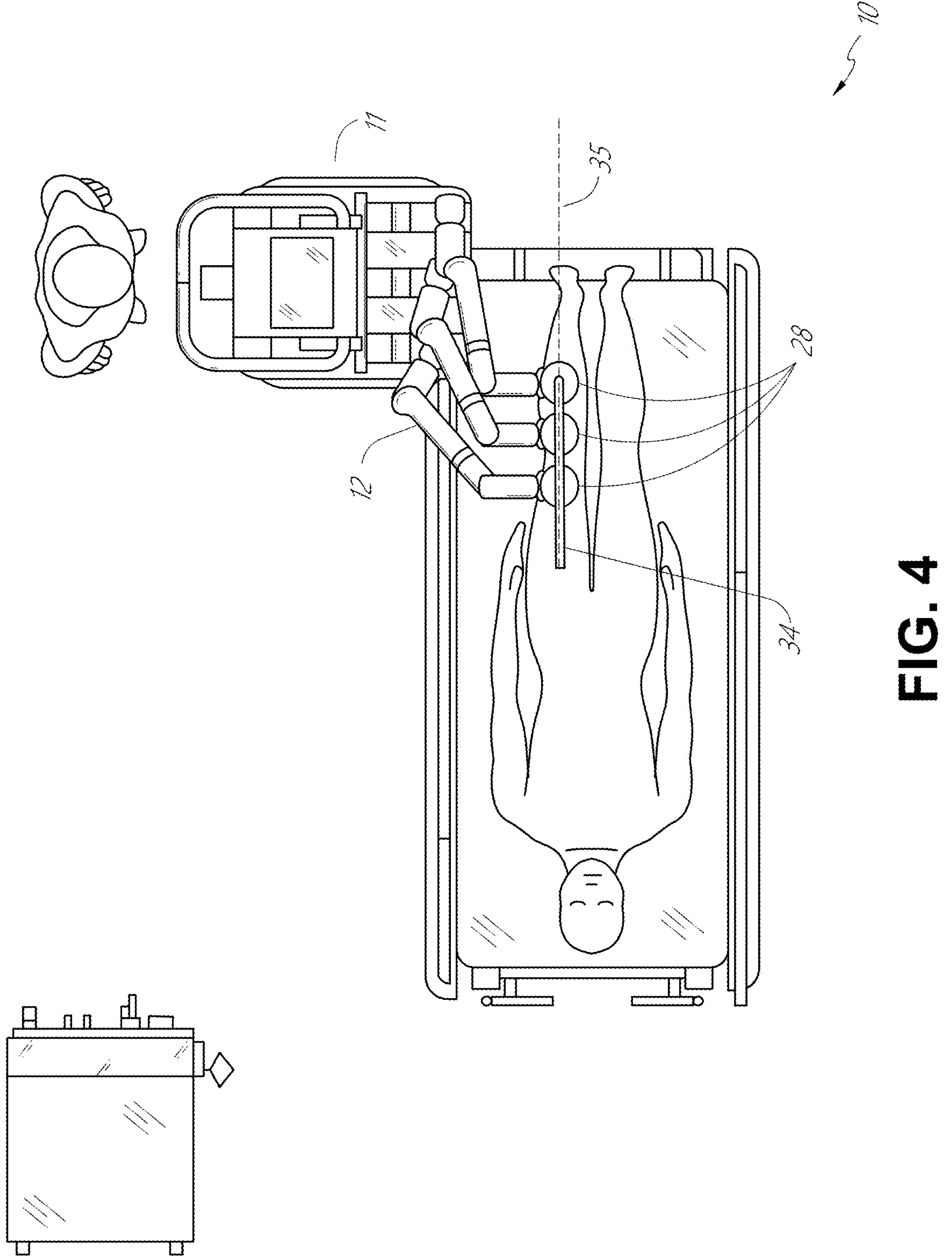
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the robotic system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
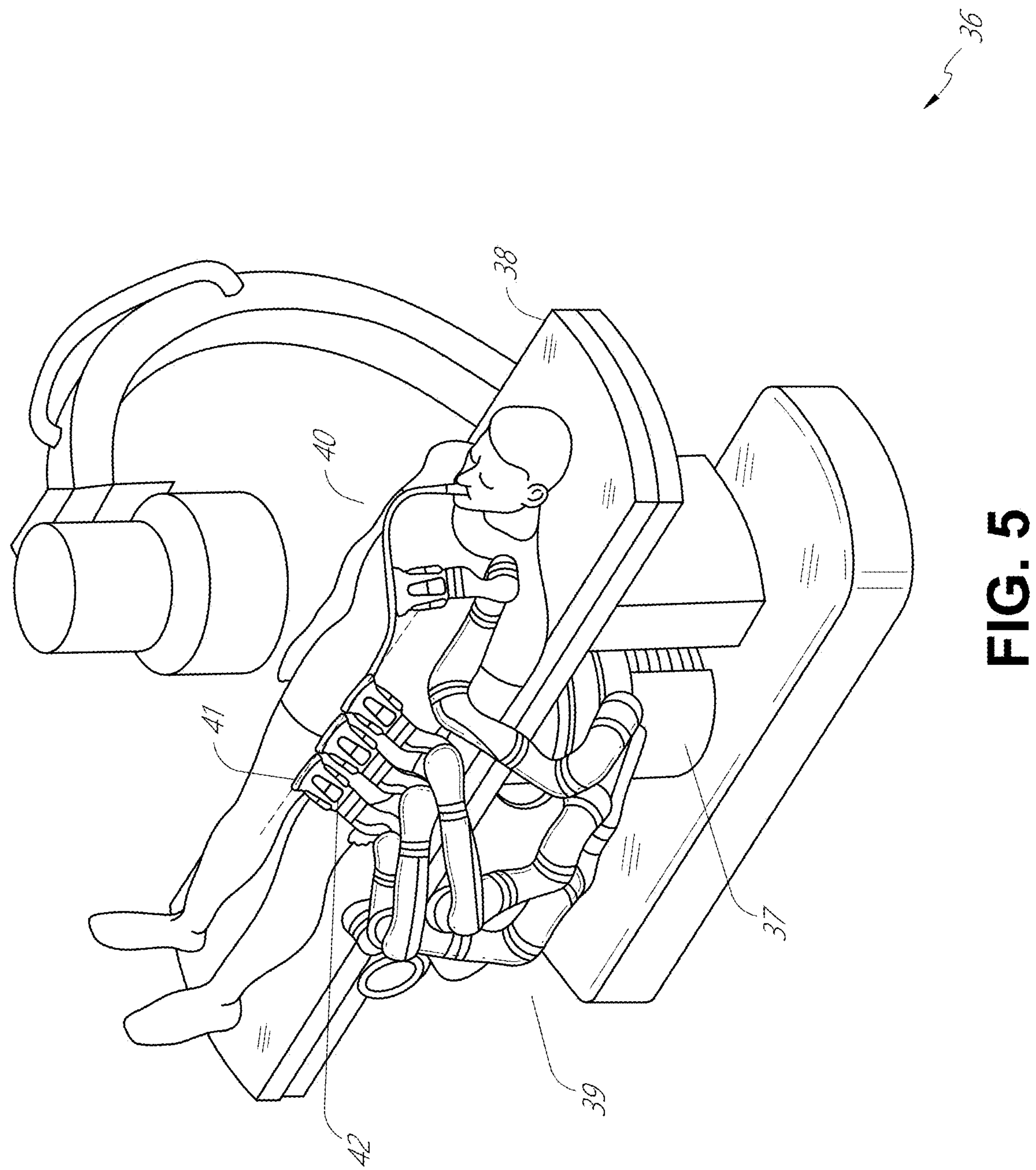
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
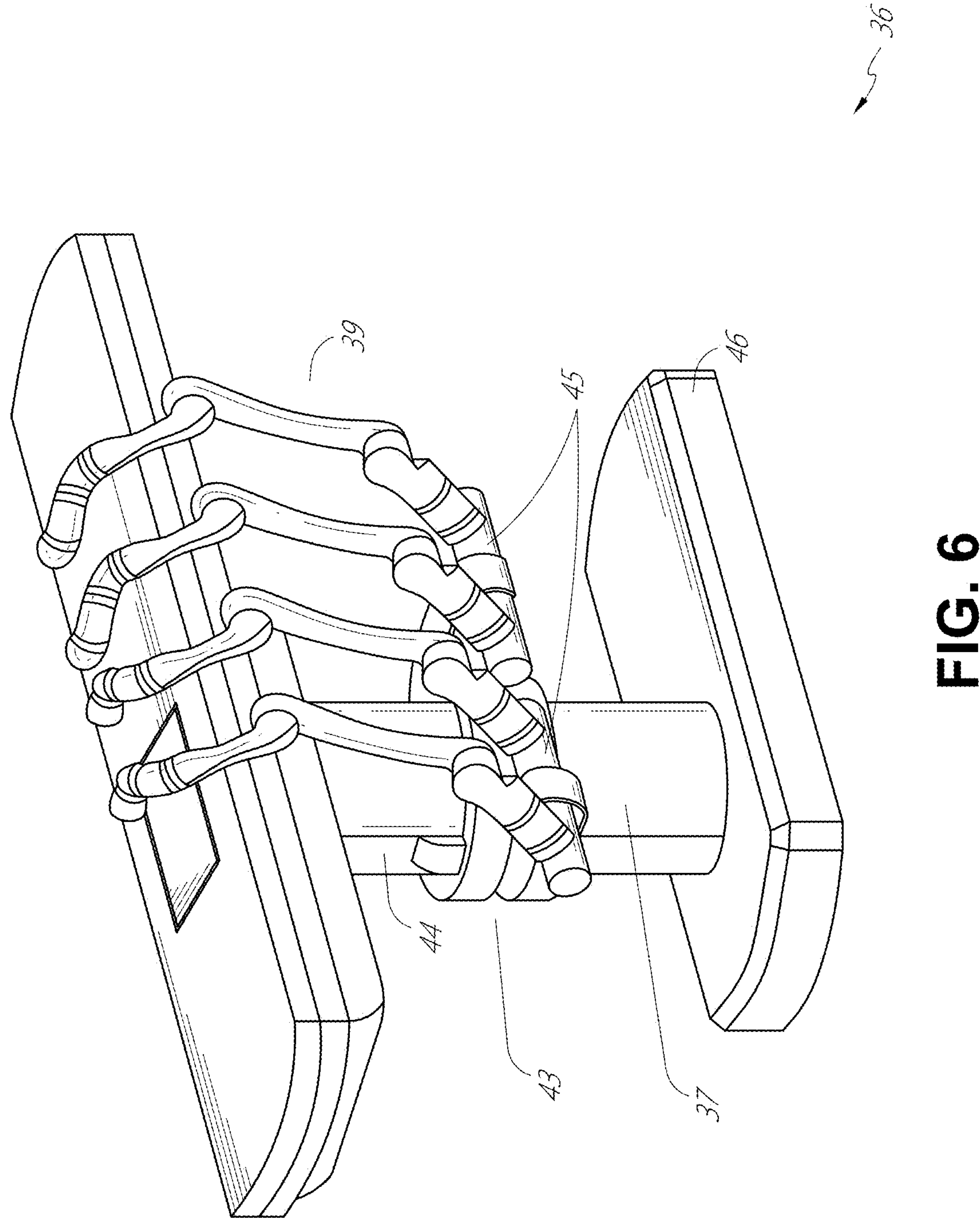
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
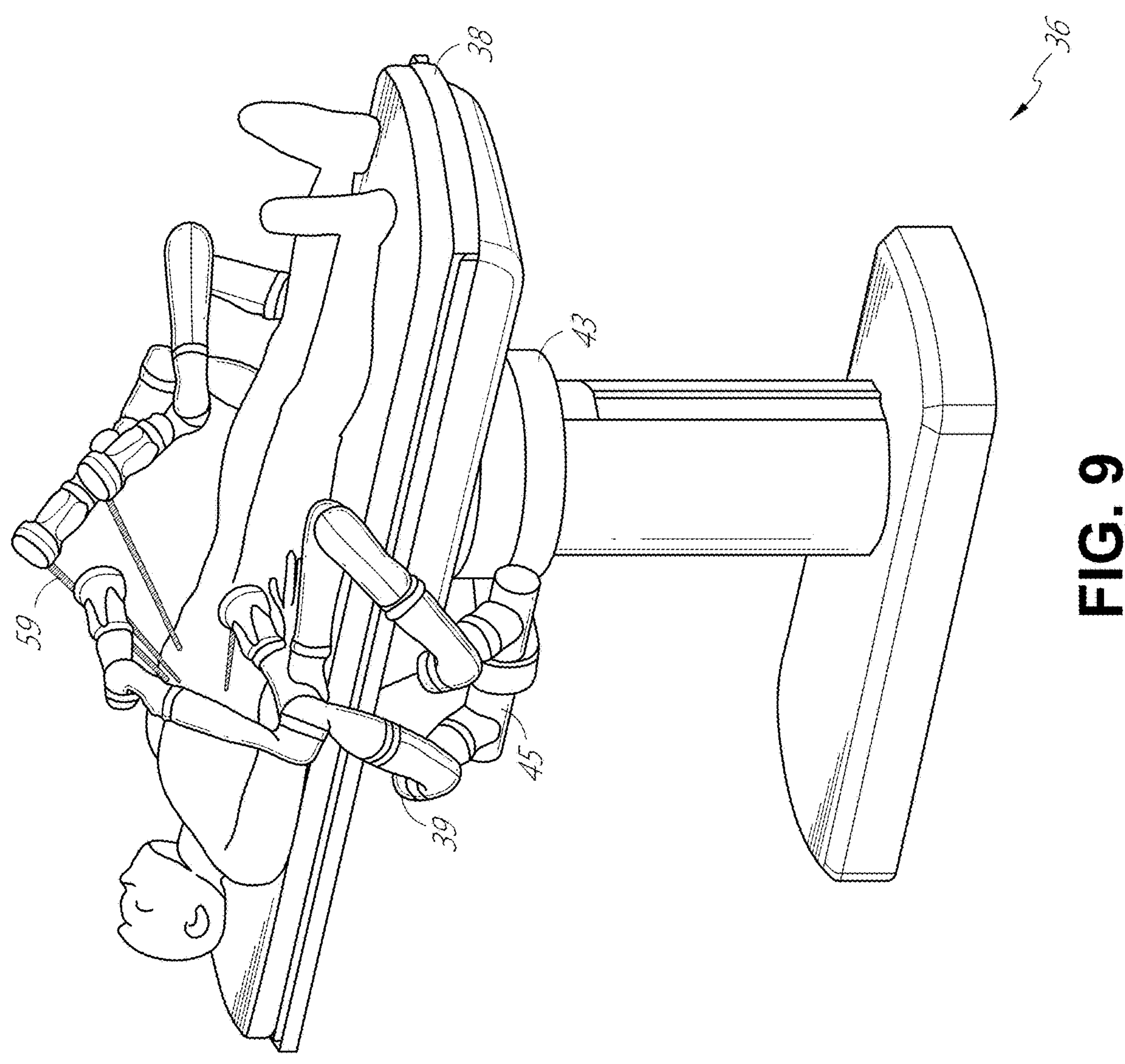
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
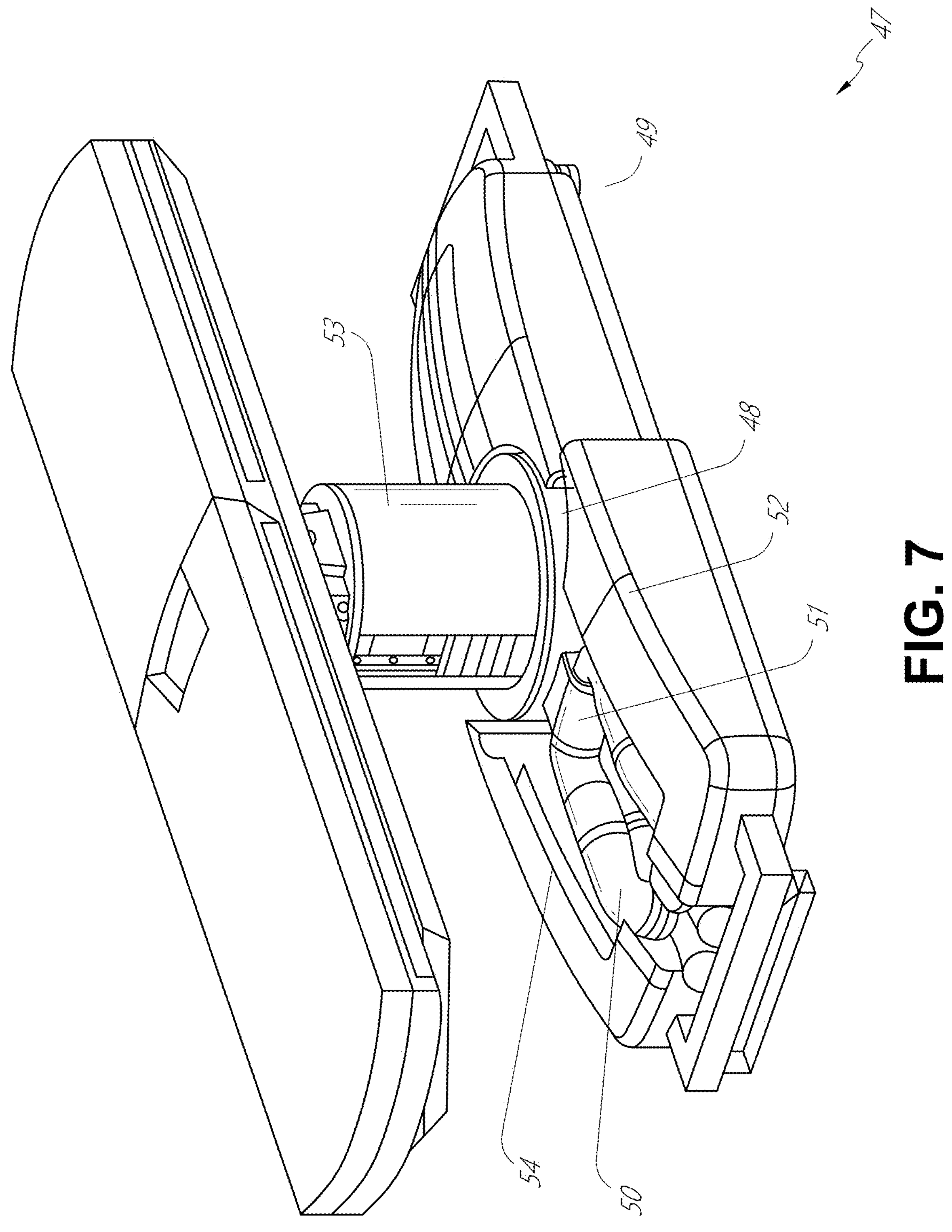
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
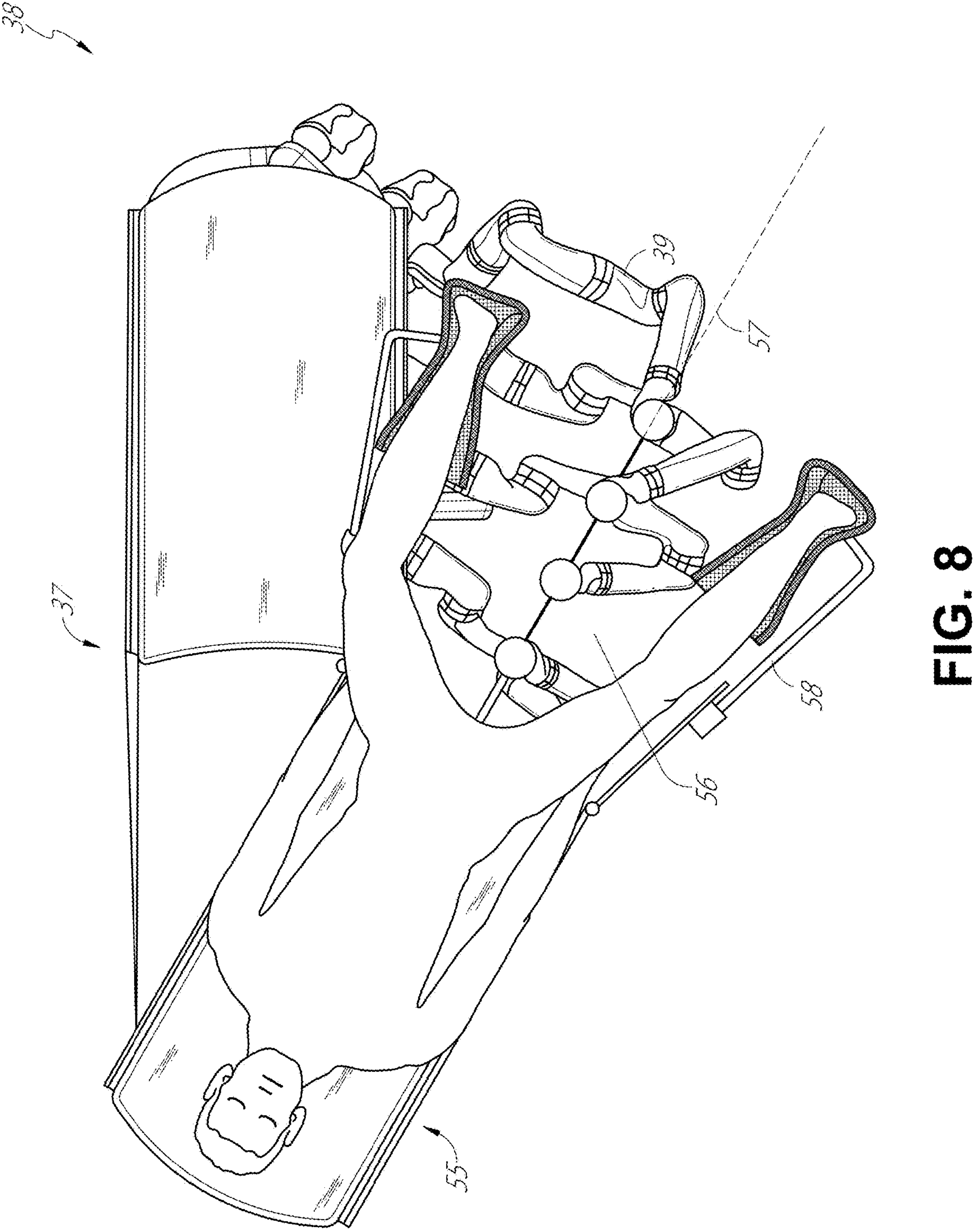
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
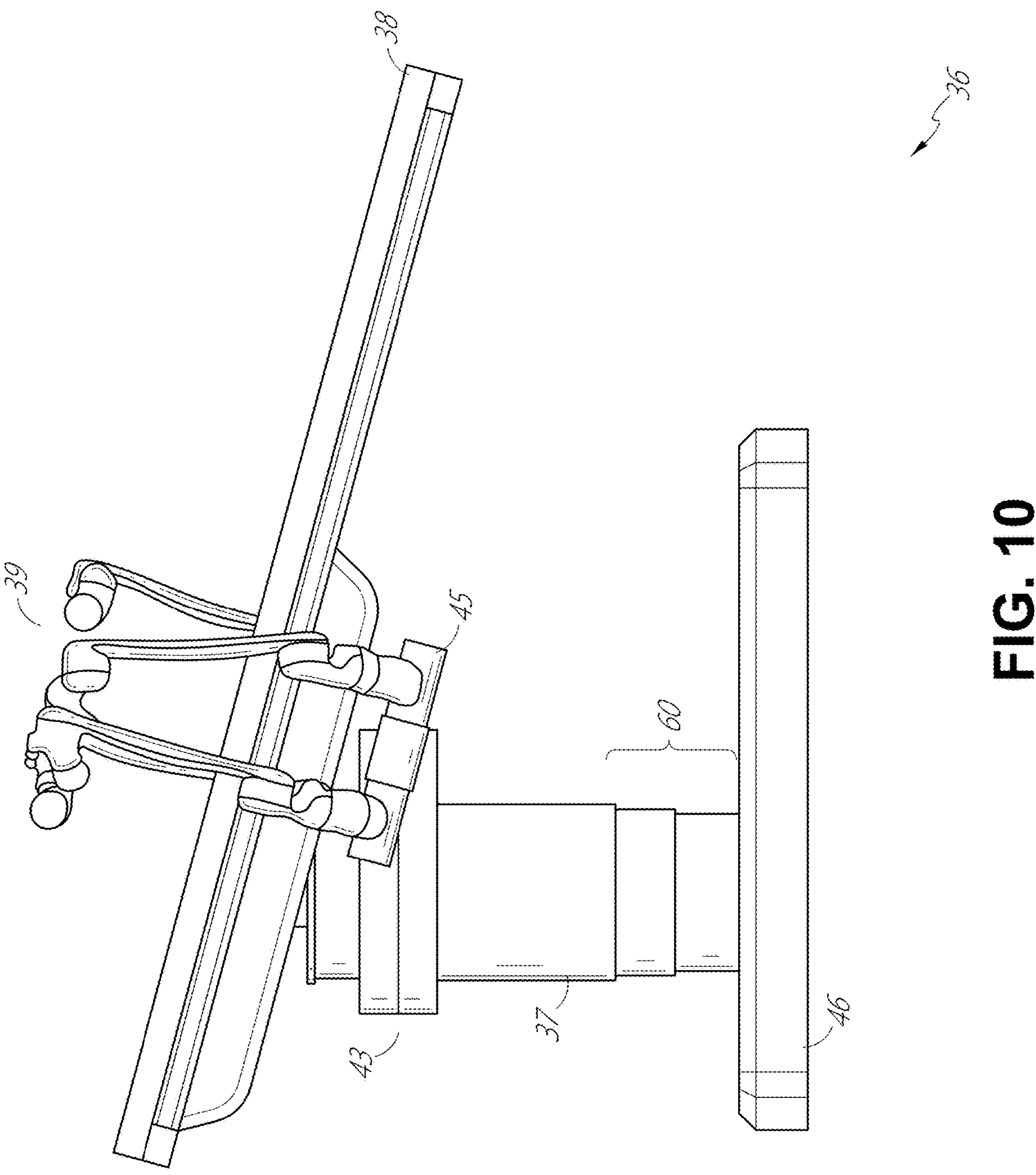
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
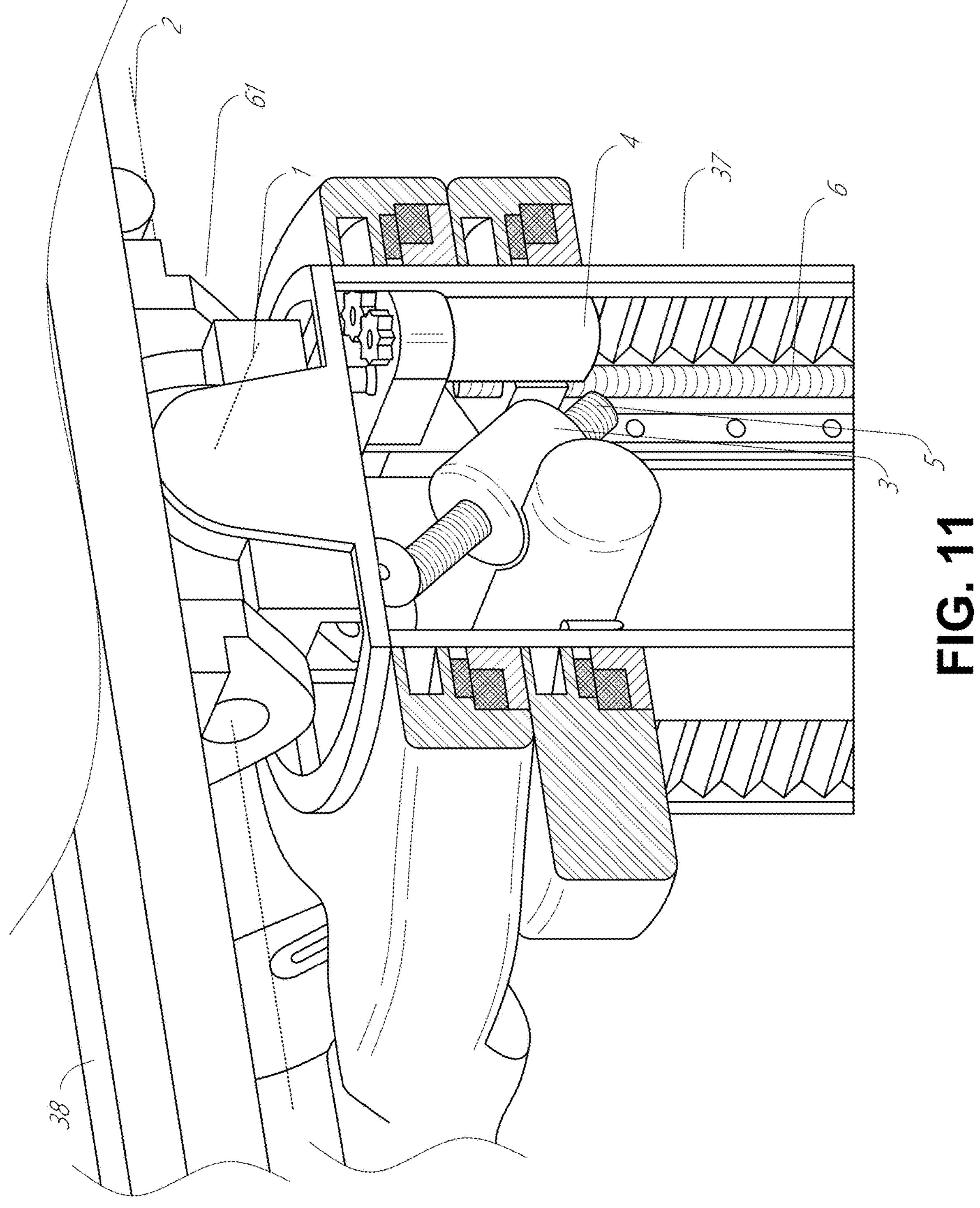
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper/higher abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
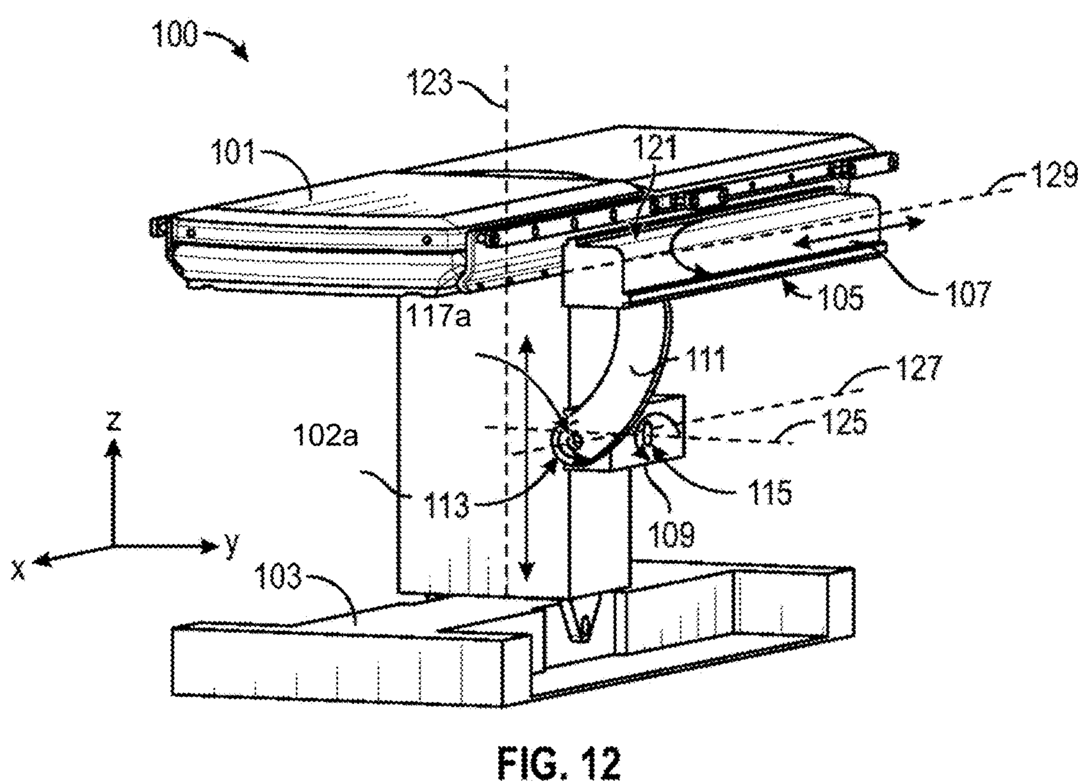
FIG. 12 illustrates an alternative embodiment of a table-based robotic system.
Figure 13:
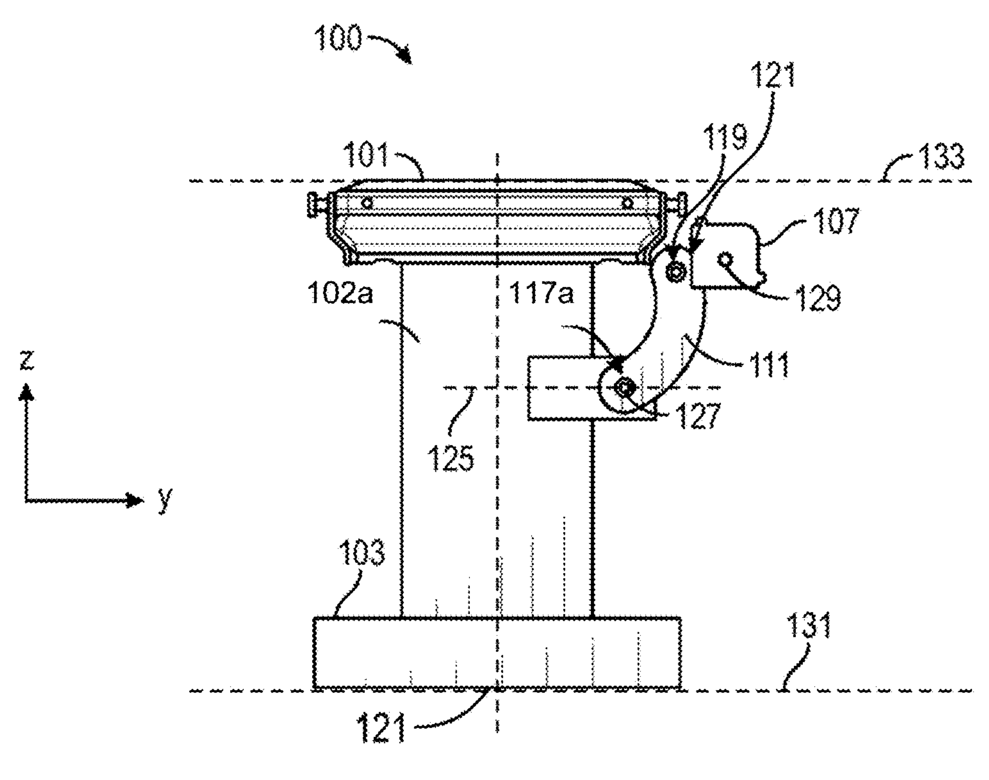
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102*a* supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102*a* that is mounted to a base 103. The base 103 and the column 102*a* support the table 101 relative to a support surface. A floor axis 131 and a support axis 133 are shown in FIG. 13.

The adjustable arm support 105 can be mounted to the column 102*a*. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102*a* by a first joint 113, which allows the carriage 109 to move relative to the column 102*a* (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117*a*, which can provide the third degree of freedom ("pivot up") for the adjustable arm support 105. An additional joint 119 (shown in FIG. 13) can be provided that mechanically constrains the third joint 117*a* to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
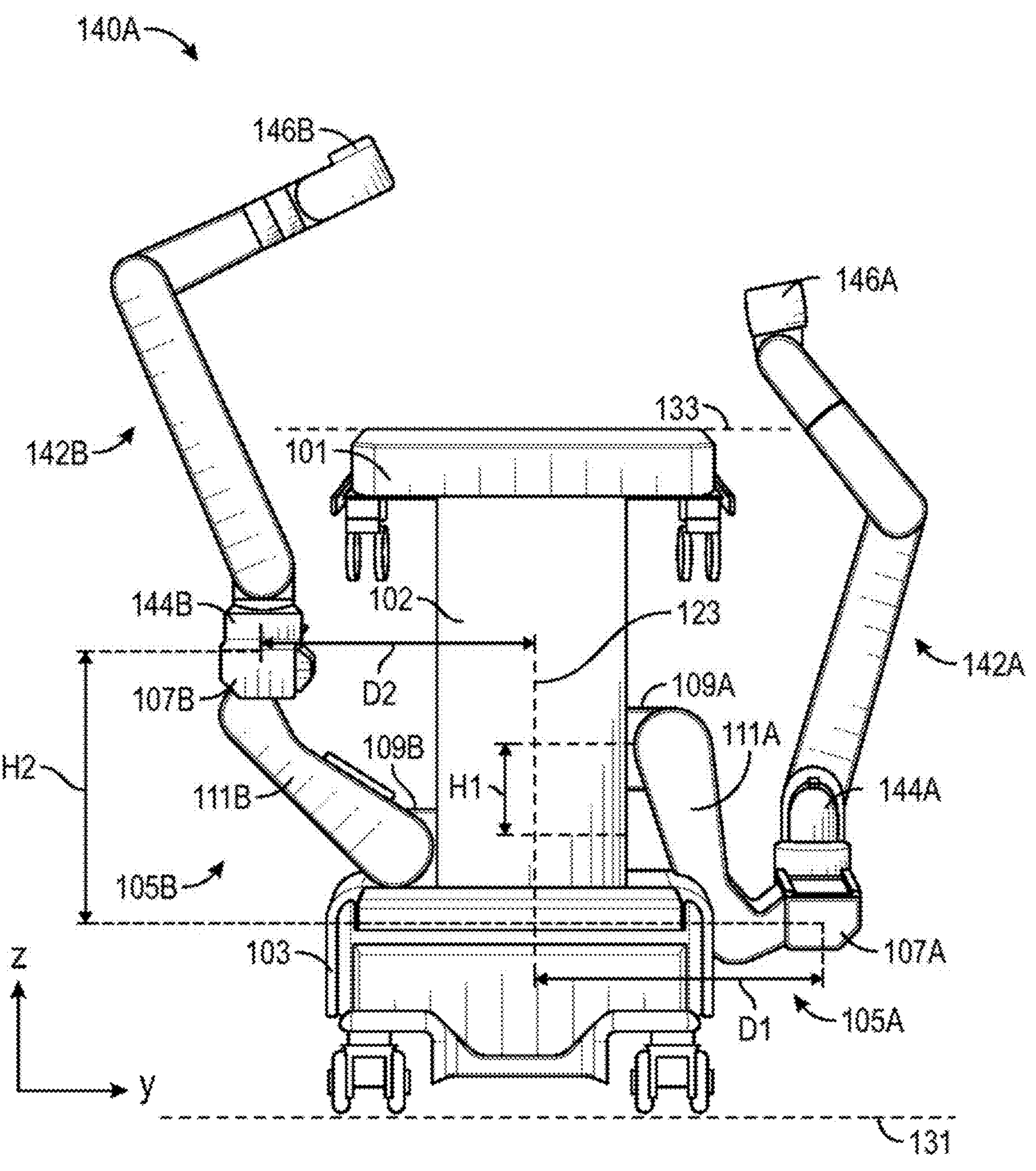
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
FIG. 15 illustrates an exemplary instrument driver.
Figure 15:
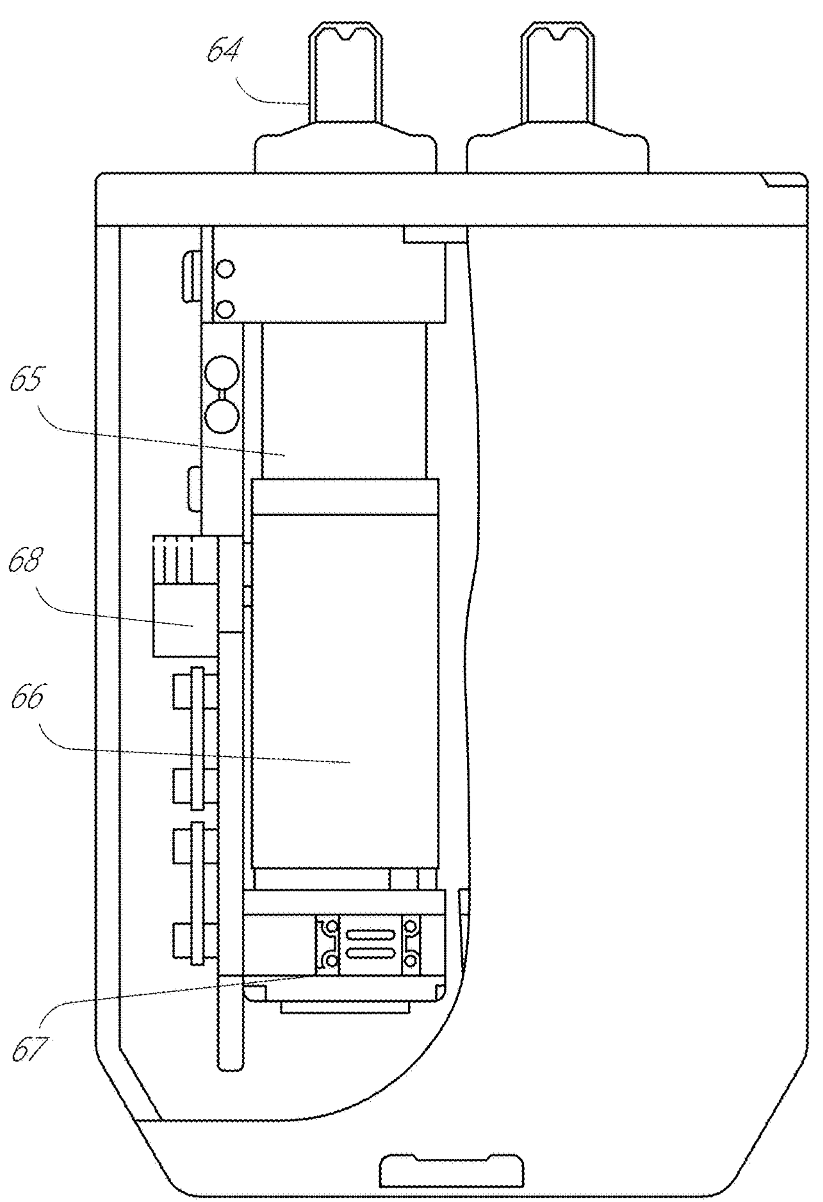
Figure 15:

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
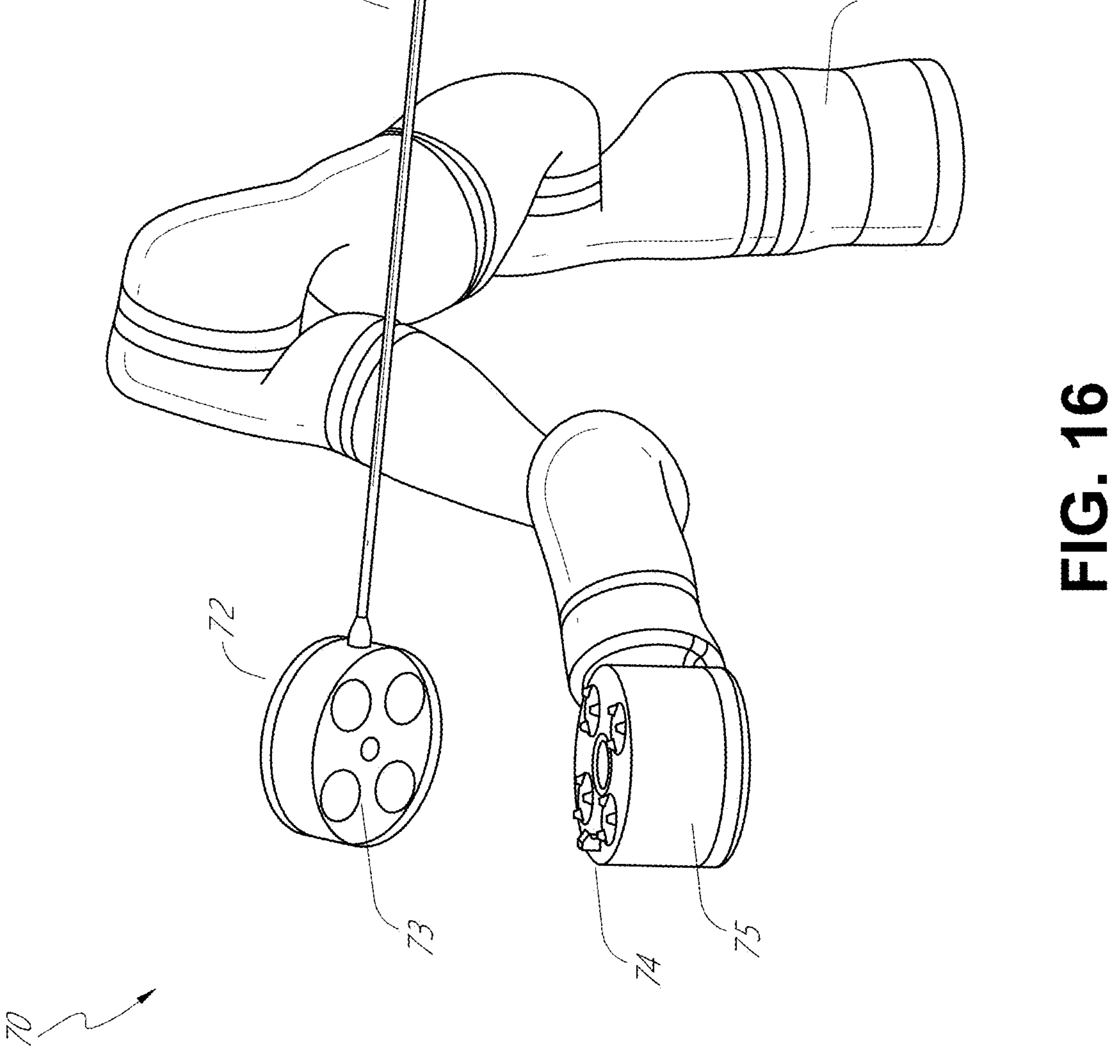
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
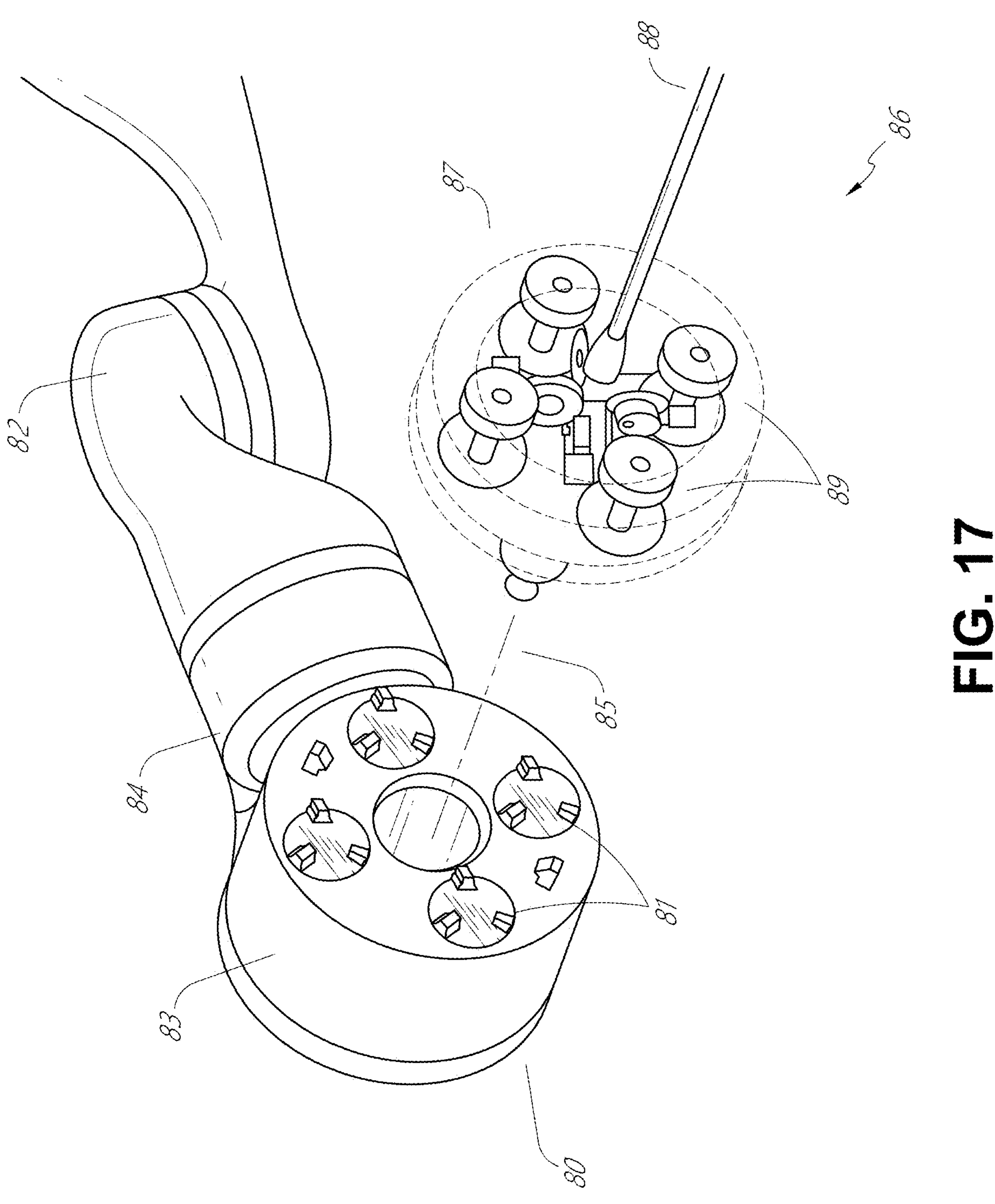
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
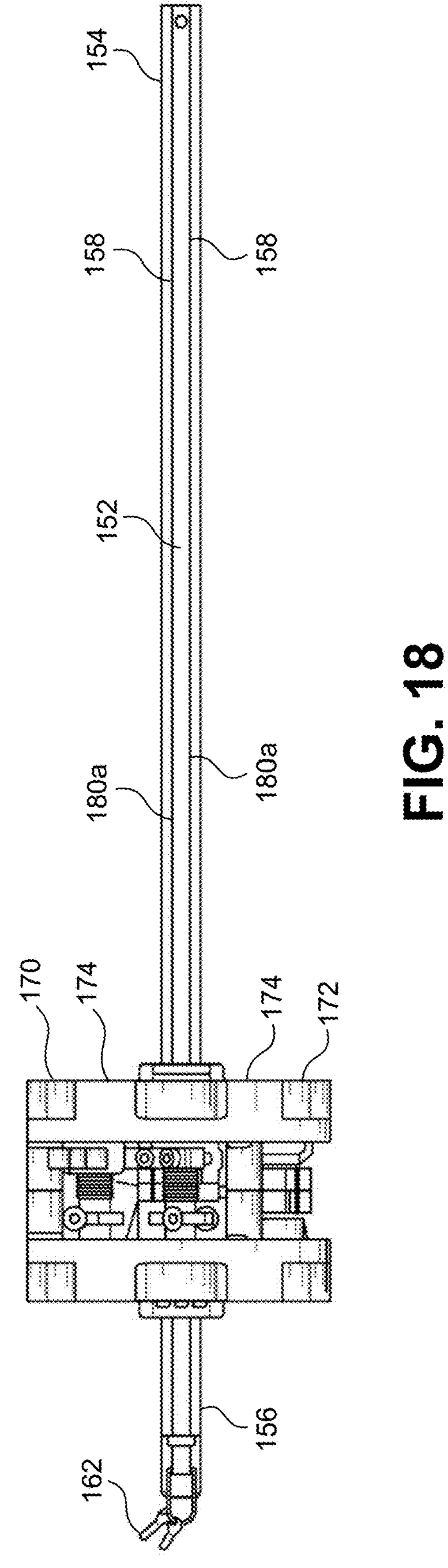
FIG. 18 illustrates an instrument having an instrument-based insertion architecture.

FIG. 18 illustrates an instrument having an instrument-based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
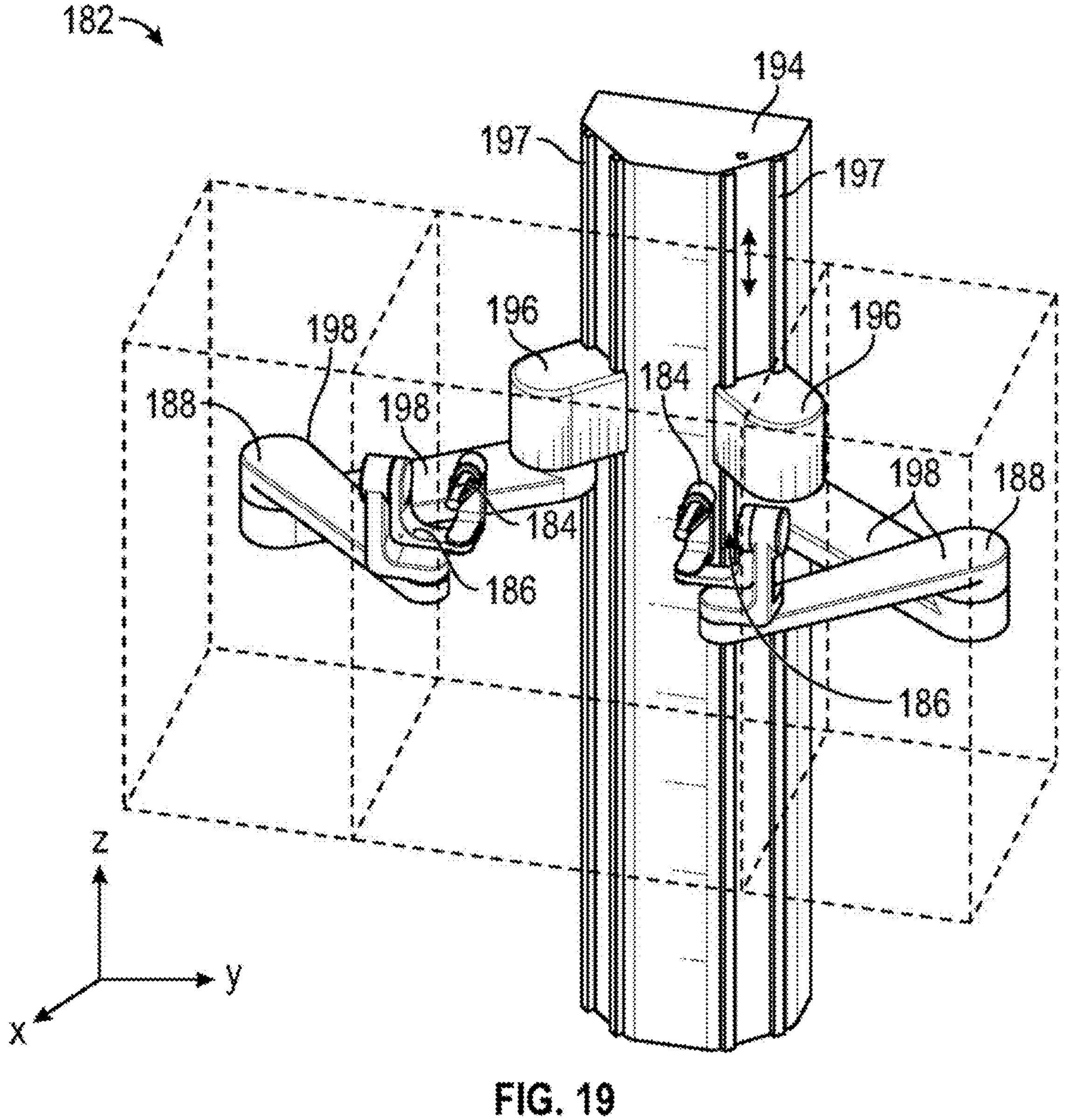
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use. In the illustrated embodiment, the controller 182 is configured to allow manipulation of two medical instruments. As illustrated, the controller 182 can include two handles 184. In some embodiments, the pair of handles 184 operates a single instrument, while in other embodiments, each of the pair of handles 184 each operates its own corresponding instrument. Each handle 184 is connected to a gimbal 186. Each gimbal is connected to a positioning platform 188. In some embodiments, the handle 184 is considered distal from the gimbal 186, which is considered distal to the positioning platform 188. The handle 184 and gimbal 186 are shown in greater detail in FIG. 22 and will be described below.

As shown in FIG. 19, in the illustrated embodiment, each positioning platform 188 includes a selective compliance assembly robot arm 198 (SCARA arm) having a plurality of links coupled to a column 194 by a prismatic joint 196. The prismatic joints 196 are configured to translate along the column 194 (e.g., along rails 197) to allow the handle 184 to be translated in the z-direction, providing a first degree of freedom. The SCARA arm 198 is configured to allow motion of the handle 184 in an x-y plane, providing two additional degrees of freedom. Thus, each of the positioning platforms 188 illustrated in FIG. 19 are configured to provide three degrees of positional or translational freedom and allow the operator to position the handles 184 at any position (within reach of the positioning platform) in three-dimensional (e.g., x, y, z) space.

In some embodiments, the column 194 (and rails 197) extends along an axis that is aligned with the vertical direction (e.g., the z-direction as illustrated) of the workspace, which can be aligned with the direction of gravity. An advantage of this positioning platform 188 is that it can provide for gravity compensation. In other words, the prismatic joint 196 of the positioning platform 188 can maintain a constant orientation of the gimbal 106 relative to the forces of gravity.

In some embodiments, the positioning platform 188 can have other configurations. For example, the positioning platform 108 need not include a prismatic joint and/or a SCARA arm in all embodiments.

In some embodiments, a load cell (not shown in FIG. 19) can be provided in a portion of the controller 182 (e.g., such as in the gimbal 186). The addition of the load cell enables the controller to have admittance control in addition to impedance control. Under admittance control, the perceived inertia of the controller 182 can be reduced. This is because mass of the gimbal 186 and/or positioning platform can be hidden via the load cell. This can be because the load cell can measure the forces imparted on the controller and be used to provide outputs that drive motors in the controller 182 to assist with the motion of the controller 182. The amount of mass that is hidden depends on the location of the load cell. In some embodiments, mass that is proximal to the load cell can be partly or substantially hidden, while mass that is distal to the load cell will not be hidden.

In some embodiments, by positioning the load cell distally on the controller 182 (e.g., in the gimbal 186 shown in FIG. 19), the mass of the gimbal 186 can be partially or substantially hidden while operating the controller 182. Likewise, the mass of the positioning platform 188 (which has a relatively higher mass than the gimbal 186) can also be partially or substantially hidden while operating the controller 182. The hidden mass advantageously results in a lower perceived inertia by a clinician. Without the load cell, in order to move the handle 184 in the z-direction, the operator supplies sufficient force to the handle 184 to lift the handle 184, the gimbal 186, and the SCARA arm 198 upward. Further, one can envision that it would require less force to move the handle in the x-y plane than to move in the z-direction. This disparity would likely result in an uneven operating experience for the operator that would make the controller 182 difficult to use. Thus, by including a load cell, as described herein, the controller 182 can assist the user in translating the handle 184 in the x-, y-, and z-directions and provide a much more even and controlled operating experience. In some embodiments, the load cell enables the positioning platform 188 to operate substantially or completely under admittance control. In contrast with the positioning platform 188, the moment of inertia of the gimbal 186 can be relatively lower. This can be because the gimbal 186 is generally much smaller than the positioning platform 188. Because of this, at least some portions of the gimbal 186 can be suitable for impedance control.

One advantage of such a hybrid impedance/admittance controller 182 as described herein is that the perceived inertia of the system can be relatively lower than systems that rely fully on impedance control. Further, the mechanical structure of the hybrid controller 182 can be simpler because the admittance control can be used to supplement and even out the movement of the system. In contrast, the mechanical structure of impedance-only systems is often very complex in an effort to normalize the forces for moving the systems in the different directions and minimize perceived inertia.

In some embodiments, by using a hybrid controller 182 as described herein, it is possible that the mass and inertia of the gimbal 186 can actually be increased relative to the gimbals of impedance-only controllers because so much of the total mass and inertia of the controller 182 can be hidden by the admittance control of the positioning platform. Increasing the size of the gimbal can, in some embodiments, allow for use of larger motors, which can allow the controller to provide stronger haptic feedback forces when compared to other systems, which necessitate the use of lightweight gimbals and motors to avoid increasing the overall mass and inertia.

As shown in FIG. 19, the hybrid controller 182 can be viewed as a plurality of links and joints in series, e.g., as a serial link manipulator. The handle 184, the gimbal 186 and the positioning platform 188 each comprise one or more links operably coupled, with the most proximal link being adjacent the column 194 of the positioning platform 188 and the most distal link being part of the handle 184 itself. In some embodiments, one or more load cells (not shown in FIG. 19) can be inserted into the controller 182 to provide admittance control of at least some portions of the controller 182. Other portions of the controller 182 can be controlled by impedance control (or in some instances, passive control) by a clinician or operator. In some embodiments, links and joints that are proximal to the load cell may be directly or indirectly affected by the load cell. Manipulation of these proximal links and joints can thus be assisted with admittance control. In some embodiments, links and joints that are distal to the load cell may not be affected, either directly or indirectly, by the load cell. Manipulation of these distal links and joints can thus be assisted with impedance control. For example, in some embodiments, a load cell is positioned in the gimbal 186 such that distal joints 128, 130, 132 (shown in FIG. 22) may not be affected directly or indirectly by the load cell. In other words, the manipulation of the axes of the gimbal 186 at these joints is not based on the output of the load cell directly or indirectly. These distal links and joints can be moved by impedance control. In contrast, links and joints that are proximal to the load cell (such as those in the positioning platform 188) may be affected directly or indirectly by the load cell. In other words, the manipulation of the axes at these joints is based on the output of the load cell directly or indirectly. These proximal links and joints can be moved by admittance control.

In some embodiments, one or more load cells are positioned in the controller. For example, in some embodiments, a load cell (not shown) is positioned in the body of each of the gimbals 106. By providing a load cell, portions of the controller 182 are capable of operating under admittance control, thereby advantageously reducing the perceived inertia of the controller while in use. In some embodiments, the positioning platform 108 is configured for admittance control, while the gimbal 106 is configured for impedance control. In other embodiments, the gimbal 106 is configured for admittance control, while the positioning platform 108 is configured for impedance control. Accordingly, for some embodiments, the translational or positional degrees of freedom of the positioning platform 108 can rely on admittance control, while the rotational degrees of freedom of the gimbal 106 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
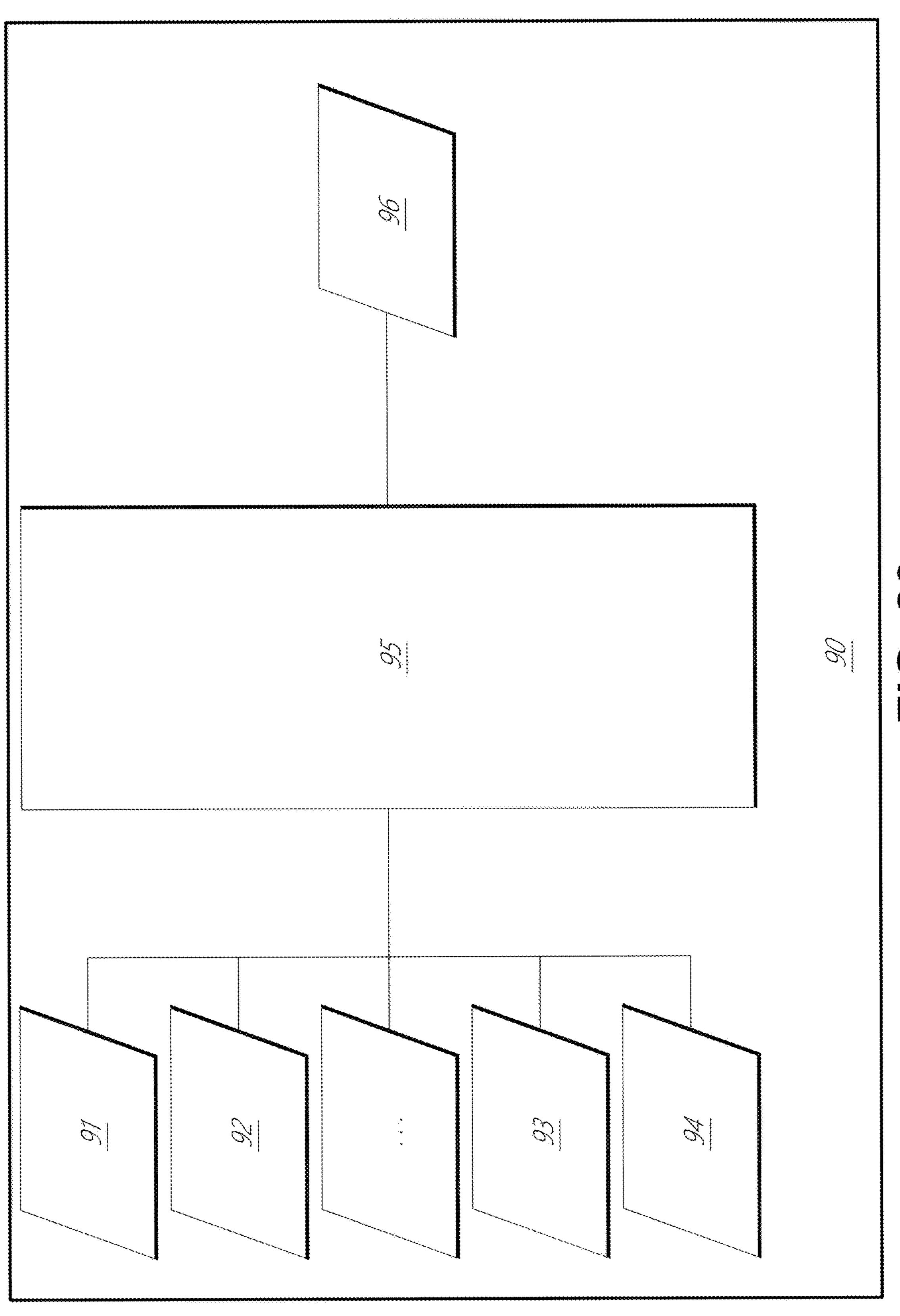
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance with an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter) may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Controllers for Robotically Enabled Teleoperated Systems

Robotically enabled teleoperated systems, such as the systems described above, can include an input device or controller that is configured to allow an operator (e.g., a physician performing a robotically enabled medical procedure) to manipulate and control one or more instruments (or robotic arms holding the one or more instruments). In some embodiments, the robotically enabled teleoperated systems comprise a controller for operating one or more medical tools. One skilled in the art will appreciate that the controllers described herein can be applied in non-medical contexts as well. For example, the controllers can be useful for manipulating tools that involve hazardous substances. In addition, in some embodiments, the controllers described herein can be useful in grabbing objects in physical and/or virtual environments. In some embodiments, the controllers can be self-sufficient as service robots interacting with human operators. In some embodiments, the controller can be coupled (e.g., communicatively, electronically, electrically, wirelessly, and/or mechanically) with an instrument (such as, e.g., a medical instrument) such that manipulation of the controller causes a corresponding manipulation of the instrument. In some embodiments, the controller and the instrument are arranged in a master-slave pair. In some embodiments, the controller may be referred to as a manipulator, emulator, master, interface, etc. In some embodiments, the controller can comprise a plurality of links assembled in parallel or in series.

The controller can serve as an input device for an operator to control the actions of a medical instrument, such as in an endoscopic, endoluminal, laparoscopic, or open surgery instrument. Movement of the controller by the operator can direct the movement of the medical instrument. For example, when an operator translates the controller in three-dimensional space (e.g., up, down, left, right, backwards, forwards), the system can cause a corresponding translation of the medical instrument. Similarly, if the operator rotates the controller (e.g., around any of three orthogonal axes), the system can cause a corresponding rotational movement of the medical instrument. The controller can also be configured to receive an input that allows the operator to actuate the medical instrument. As one example, if the medical instrument includes a grasper, the controller can receive an input that allows the operator to open and close the grasper.

The controller can also provide haptic feedback to the operator. For example, in some embodiments, forces or torques imparted on the medical instrument can be transmitted back to the operator through the controller. In some embodiments, providing haptic feedback to the operator through the controller provides the user with an improved operating, controlling, or driving experience. In some embodiments, to make it easier for the operator to interact with the controller and operate the system, haptic cues can be provided.

In some embodiments, the controller is also used to align the operator's hands with the orientation of a medical instrument, for example, when switching medical instruments. For example, if a medical instrument is positioned within a patient during a medical procedure, it is important that the medical instrument does not move unexpectedly or unintentionally. Thus, when an operator desires to take control of a medical instrument already positioned within the patient, the controller can first move to match the orientation of the medical instrument, while the instrument remains in place. With the controller correctly oriented to match the orientation of the medical instrument, the operator can then use the controller to manipulate the medical instrument.

In some embodiments, robotically enabled medical systems include controllers with seven degrees of freedom that follow the operator's hand movement, with the seven degrees of freedom including three positional degrees of freedom (e.g., translational movement in x, y, z space), three rotational degrees of freedom (e.g., rotational movement around pitch, roll, and yaw axes), and one (or more) instrument actuation degree of freedom (e.g., an angular degree of freedom). In some embodiments, the instrument actuation degree of freedom can control the opening and closing of an end effector of the medical instrument, such as a gripper or grasper to hold an object. In some embodiments, the instrument actuation degree of freedom may be omitted. In some embodiments, controllers may include greater or fewer numbers of degrees of freedom. For example, in some embodiments, a controller may include more than three positional degrees of freedom or more than three rotational degrees of freedom to provide one or more redundant degrees of freedom. In some embodiments, redundant degrees of freedom may provide additional mechanical flexibility for the controller, for example, to avoid singularities caused by the mechanical structure of the controller.

Figure 21A:
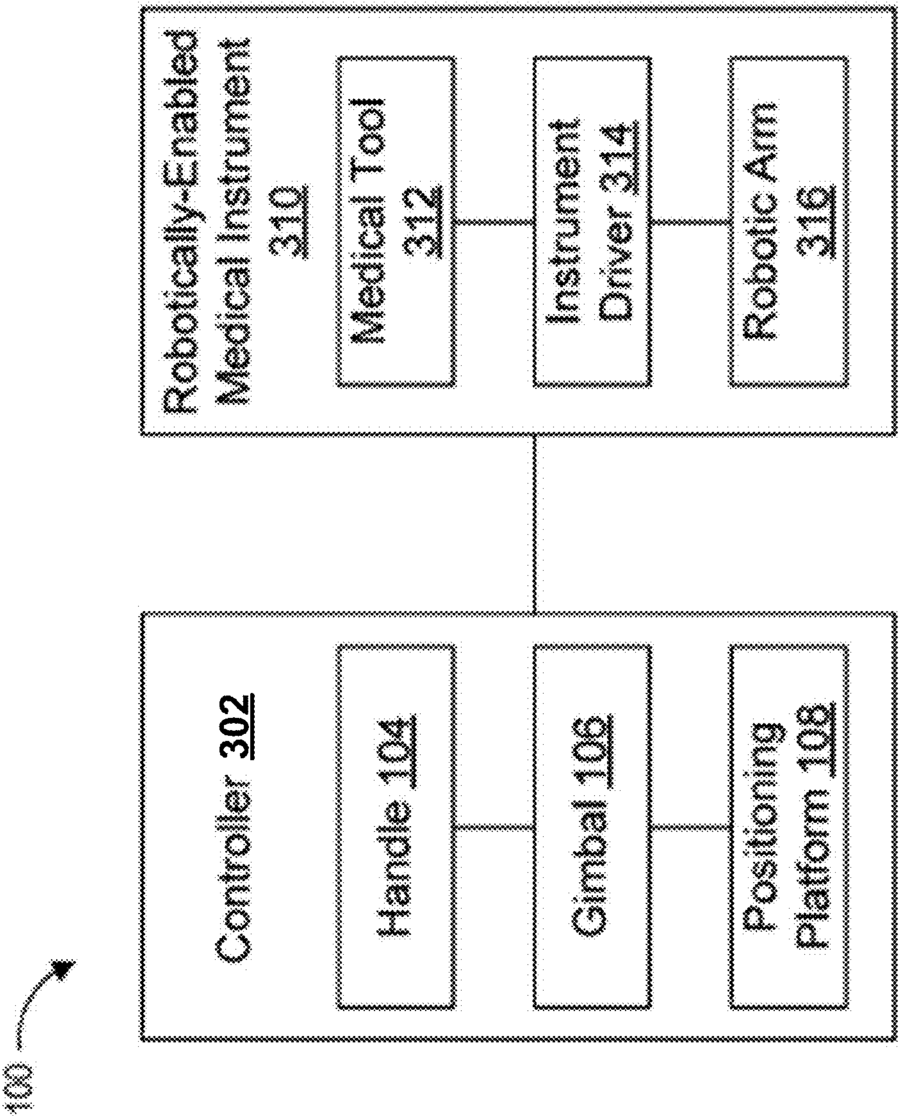
FIG. 21A is a block diagram illustrating an embodiment of a robotically enabled medical system including a controller for a robotically enabled medical instrument.

FIG. 21A illustrates a block diagram of an embodiment of a robotically enabled medical system 100 including a schematic representation of an embodiment of a controller 302 and schematic representation of an embodiment of a robotically enabled medical instrument 310. As briefly mentioned above, the controller 302 can be coupled (e.g., mechanically, electrically, or functionally) with the robotically enabled medical instrument 310 such that manipulation of the controller 302 causes a substantially corresponding movement of the robotically enabled medical instrument 310, and forces imparted on the robotically enabled medical instrument 310 can be transmitted back to the controller and haptically communicated to the operator. In some embodiments, the controller 302 and the robotically enabled medical instrument 310 are arranged in a master-slave configuration.

In the illustrated embodiment of the system 100, the controller 302 includes a handle 104, a gimbal 106, and a positioning platform 108. The handle 104 can be configured to be held by the operator. As illustrated, in some embodiments, the handle 104 is coupled to the gimbal 106 and the positioning platform 108. As noted above, the handle 104 can include one or more degrees of freedom to actuate an instrument. The gimbal 106 can be configured to provide one or more rotational degrees of freedom to allow the operator to rotate the handle 104. In some embodiments, the gimbal 106 is configured to provide at least three rotational degrees of freedom. For example, the gimbal 106 can be configured to allow the operator to rotate the handle 104 about pitch, roll, and yaw axes. Example gimbals 106 are described in greater detail with respect to FIGS. 17-19B. The positioning platform 108 can be configured to provide one or more translational (also referred to herein as positional) degrees of freedom to allow the operator to translate the handle 104. In some embodiments, the positioning platform 108 is configured to provide at least three positional degrees of freedom. For example, the positioning platform 108 can be configured to allow the operator to translate the handle 104 in three-dimensional space (e.g., x-, y-, and z-directions). An example positioning platform 108 is described in greater detail with respect to FIG. 19. Together, the gimbal 106 and the positioning platform 108 can enable the user to manipulate the handle 104.

In the illustrated embodiment, the robotically enabled medical instrument 310 includes an instrument or tool 312 (which may include an end effector), an instrument driver 314, and a robotic arm 316 (or other instrument positioning device). The medical tool 312 can be, for example, the laparoscopic instrument 59 shown in FIG. 9 above, as well as other types of endoscopic or laparoscopic medical instruments as described throughout this application and as will be apparent to those of ordinary skill in the art. The medical tool 312 can include an end effector or a plurality of end effectors. The end effector can be positioned on a distal end of the medical tool 312. The end effector can be configured for insertion into the patient's body. In some embodiments, the end effector can be a grasper, a gripper, a cutter, a basketing apparatus, or a scissor, among many others. In some embodiments, the medical tool 312 can comprise a scope or a camera.

The medical tool 312 can be attached to the instrument driver 314. The instrument driver 314 can be configured to actuate the medical tool 312 as described above. For example, the instrument driver 314 can be configured to pull one or more pull wires of the medical tool 312 to actuate the medical tool 312. In some embodiments, the instrument driver 314 can be an instrument drive mechanism as described above. The instrument driver 314 can be attached to the robotic arm 316, for example, as shown in FIG. 14. The robotic arm 316 can be configured to articulate or move to further manipulate and position the medical tool 312. Example medical instruments/tools, instrument drivers, and robotic arms are shown in the systems of FIGS. 1-15, described above.

The controller 302 can be coupled to the robotically enabled medical instrument 310 such that manipulation of the handle 104 causes substantially corresponding movement of the medical tool 312 and forces imparted on the medical tool 312 can be haptically transmitted to the operator through the handle 104. Manipulation of the handle 104 can be measured or determined by measuring forces and movements of the gimbal 106 and the positioning platform 108. Movement of the medical tool 312 can be caused by articulation and movement of the instrument driver 314 and/or the robotic arm 316. Thus, by manipulating the handle 104, the operator can control the medical tool 312.

As will be described below, in some embodiments, the controllers described herein are configured to operate with both admittance and impedance control. These and other features of the controllers are further discussed in the following sections.

A. Hybrid Controllers.

Figure 21B:
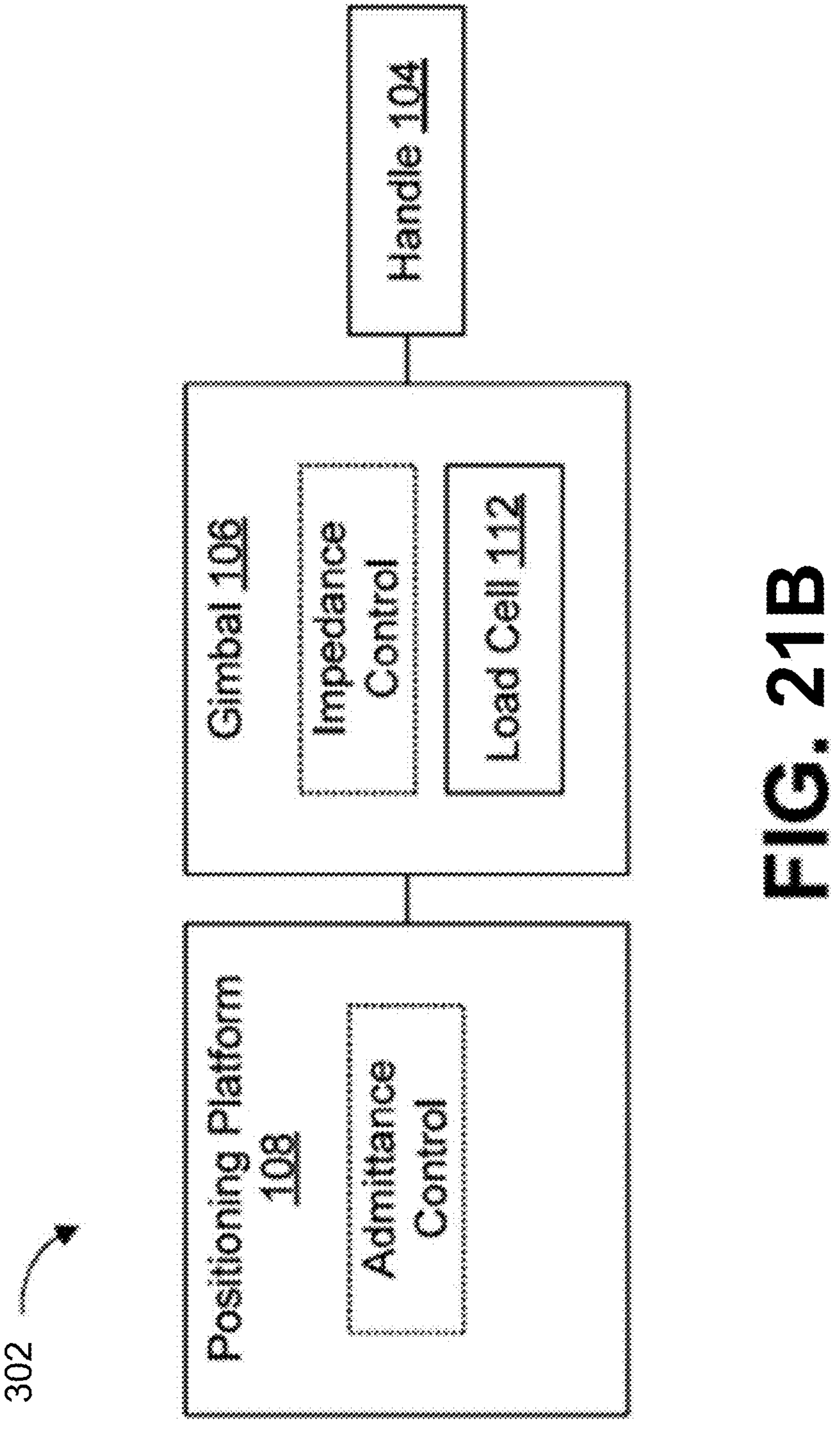
FIG. 21B is a block diagram illustrating an embodiment of the controller of FIG. 21A, which can be configured for hybrid impedance and admittance control.

FIG. 21B is a block diagram of an embodiment of a controller 302 configured to operate using both impedance and admittance control. Such a controller 302 can be referred to as a hybrid controller. However, in some embodiments, a controller configured to operate using impedance control only (without admittance control) or admittance control only (without impedance control) may be used.

Impedance control and admittance control are two control schemes for controlling a robotic system. Under impedance control, the system measures displacements (e.g., changes in position and velocity) and outputs forces. For example, for impedance control, the system can measure how far or fast an operator moved the controller, and, based on the measurement, generate forces on the controller (e.g., by actuating motors). Under impedance control, the operator's movement of the controller may back drive portions of the instrument. In many cases, the use of impedance control can result in a large perceived inertia. This can be because, for example, impedance control relies on the operator moving the controller. Under impedance control, the operator overcomes the perceived mass or inertia of the controller in order to move it, causing the controller to feel heavy. For impedance control, the operator physically overcomes most or all of the inertia in the system in order to move the controller. Some controllers rely solely on impedance control.

Under admittance control, the system measures forces and/or torques imparted on the controller by the operator and outputs corresponding velocities and/or positions of the controller. In some respects, admittance control is the opposite of impedance control. In some embodiments, the use of admittance control can result in a decrease in the perceived inertia or mass of a system. Admittance control can be used to change the dynamics of a controller that is perceived as having a high mass or inertia. In some instances, by using admittance control, the operator need not overcome all of the inertia in the system to move the controller. For example, under admittance control, when a user imparts a force on the controller, the system can measure the force and assist the user in moving the controller by driving one or more motors associated with the controller, thereby resulting in desired velocities and/or positions of the controller. Stated another way, for admittance control, a force sensor or load cell measures the force that the operator is applying to the controller and moves the controller as well as the coupled robotically enabled medical instrument 310 in a way that feels light. Admittance control may feel lighter than impedance control because, under admittance control, one can hide the perceived inertia of the controller because motors in the controller can help to accelerate the mass. In contrast, with impedance control, the user is responsible for all or substantially all mass acceleration.

As shown in the illustrated embodiment in FIG. 21B, the controller 302 includes a handle 104, a gimbal 106, and a positioning platform 108. As described above, the gimbal 106 can be configured to provide one or more rotational degrees of freedom (e.g., three or four), and the positioning platform 108 can be configured to provide one or more rotational degrees of freedom (e.g., three or four). The gimbal 106 and the positioning platform 108 can allow the user to move the handle 104 in three-dimensional space and rotate the handle 104 around pitch, roll, and yaw axes. Manipulation of the handle 104 results in movement of a corresponding medical instrument. Further, the handle 104, gimbal 106, and positioning platform 108 can be configured to provide haptic feedback to the operator representative of forces imparted on the medical instrument.

As illustrated by the dashed boxes in FIG. 21B, in some embodiments, in the controller 302, the gimbal 106 is configured for impedance control and the positioning platform 108 is configured for admittance control. Accordingly, for some embodiments, the translational or positional degrees of freedom of the positioning platform 108 rely on admittance control, while the rotational degrees of freedom of the gimbal 106 rely on impedance control. As described further below, this type of hybrid controller 302 can have certain advantages. In other embodiments, the gimbal 106 is configured for admittance control and the positioning platform 108 is configured for impedance control. In some embodiments, the gimbal 106 and the positioning platform can be both be configured for admittance control or both be configured for impedance control.

To utilize admittance control, the controller 302 includes at least one force sensor or load cell 112. The load cell 112 is configured to measure forces imparted on the controller 302 (generally, forces imparted on the handle 104) by the operator. The output signal of the load cell 112 (a measure of force) is used to provide control signals that control movement of the controller 302, such as the positioning platform 108. The robotically enabled medical instrument 310 will follow the motion of the handle 104 (e.g., by activating one or more motors in the instrument driver 314 or the robotic arm 316). In some embodiments, the load cell 112 can be a three degree of freedom load cell, which measures forces in three directions.

Figure 22:
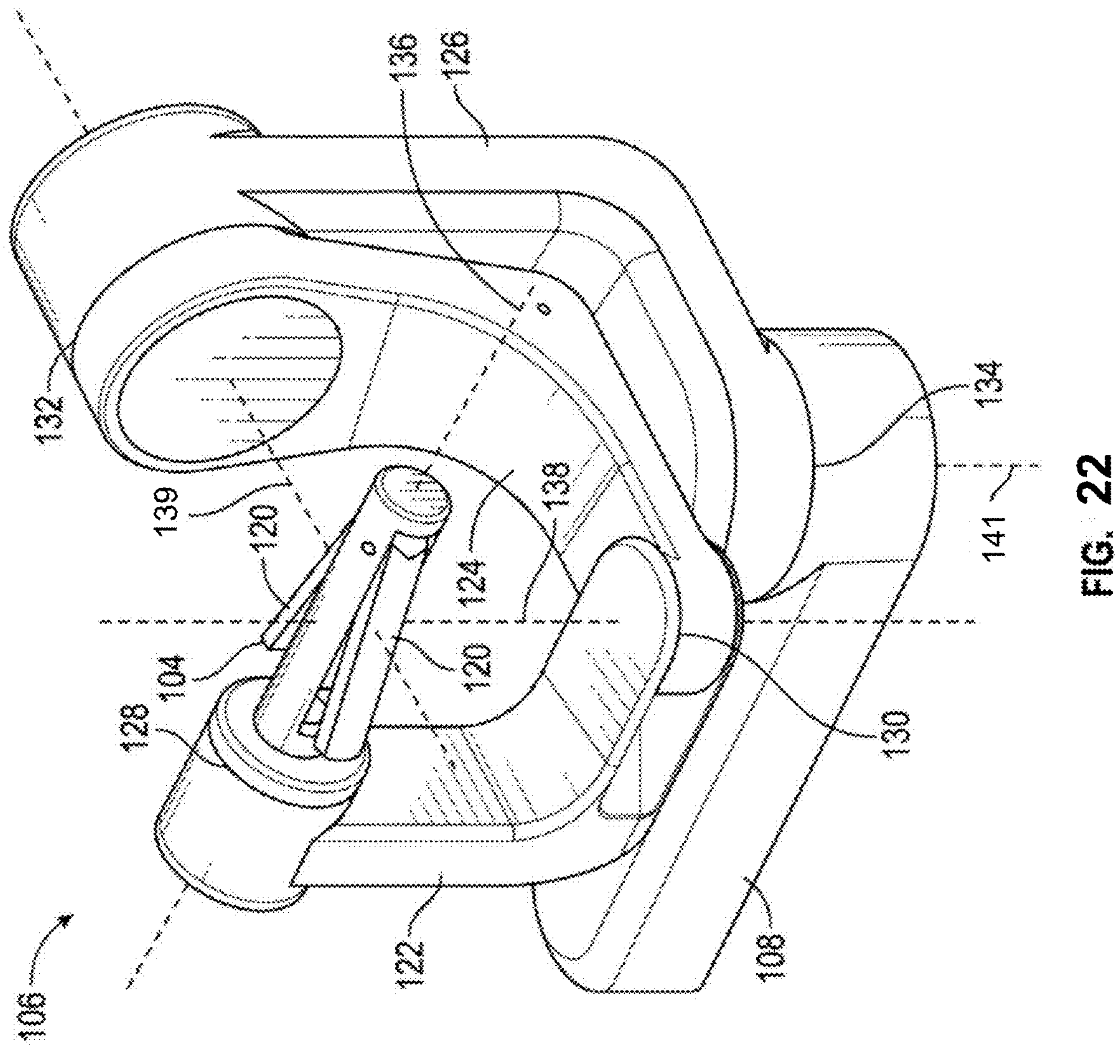
FIG. 22 is an isometric view of an embodiment of a gimbal for a controller.

In the illustrated embodiment, the load cell 112 is positioned within the gimbal 106. FIG. 22, described below, shows different locations where the load cell 112 can be positioned within the gimbal 106. Other positions for the load cell 112 are also possible. In some embodiments, the load cell 112 is positioned in the positioning platform 108. In some embodiments, more than one load cell 112 is included (e.g., two, three, four, or more load cells), which can be positioned in the handle 104, the gimbal 106, and/or the positioning platform 108.

In some embodiments, the load cell 112 is positioned distally (closer to the handle 104) in the controller 302. In some embodiments, this allows the use of the admittance control to hide the perceived mass of the portions of the controller 302 that are located proximally of the load cell 112 (e.g., the portions of the controller 302 that are located on the opposite side of the load cell 112 from the handle 104).

As mentioned above, in some embodiments, the load cell 112 (or force sensor) is positioned in the gimbal 106. In some embodiments, the gimbal 106 provides the rotational degrees of freedom for the controller 302 with impedance control, while the positioning platform 108 provides the positional degrees of freedom for the controller 302 with admittance control (e.g., based on the output of the load cell 112 positioned in the gimbal 106). There are many ways the load cell 112 can be positioned within the gimbal 106. The degree that a perceived inertia of a controller 302 is reduced can be based in part on the location of the load cell 112 within the gimbal 106. Two example embodiments showing a load cell 112 positioned in two different portions of a gimbal 106 are described in this section. Other embodiments are also possible.

FIG. 22 is an isometric view of an embodiment of a gimbal 106. As illustrated, for some embodiments, the gimbal 106 is positioned at the distal end of the positioning platform 108 (only the last link of the positioning platform 108 is illustrated in FIG. 22). As used in this application, in the context of the controller 302, the term distal refers to a direction toward the handle 104 (e.g., the handle 104 is the distal-most component of the controller 302) and the term proximal refers to the opposite direction. Accordingly, a proximal end of the gimbal 106 can be attached to the distal end of the positioning platform 108. Further, the handle 104 can be positioned at the distal end of the gimbal 106.

In some embodiments, the handle 104 is configured to be held by the operator. The handle 104 can be configured to simulate or mimic the medical instrument that the controller 302 is used to control. In some embodiments, the handle comprises a grasper handle (e.g., a radially symmetric grasper handle), a stylus, a paddle-type handle, etc. In the illustrated embodiment, the handle 104 includes two actuation arms 120 configured to provide the instrument actuation degree of freedom discussed above. While holding the handle 104, the operator can adjust an angle between the actuation arms 120 to control a corresponding angle associated with the controlled medical instrument. For example, in a case where the medical instrument is a grasper, shears, etc., the angle between the actuation arms 120 can be used to control the angle between two jaws of the grasper.

In the illustrated embodiment, the gimbal 106 comprises three arms or links connected by joints. Arranged distally to proximally and as illustrated in FIG. 22, the gimbal 106 comprises a first link 122, a second link 124, and a third link 126. Arranged distally to proximally and as illustrated in FIG. 22, the gimbal 106 also comprises a first joint 128, a second joint 130, a third joint 132, and a fourth joint 134. The joints allow the various links to rotate, providing the gimbal 106 with the rotational degrees of freedom discussed above.

The handle 104 is connected to the distal end of the first link 122 by the first joint 128. The first joint 128 can be configured to allow the handle 104 to rotate relative to the first link 122. In the illustrated embodiment, the first joint 128 allows the handle 104 to rotate around a roll axis 136. In some embodiments, the roll axis 136 is aligned with a longitudinal axis of the handle 104. The first joint 128 can be a revolute joint.

The proximal end of the first link 122 is connected to the distal end of the second link 124 by the second joint 130. The second joint 130 can be configured to allow the handle 104 and the first link 122 to rotate relative to the second link 124. In the illustrated embodiment, the second joint 130 allows the handle 104 and the first link 122 to rotate around a yaw axis 138. In some embodiments, the yaw axis 138 extends through the second joint 130 and intersects with the roll axis 136 at a center point of the handle 104. The second joint 130 can be a revolute joint. As shown, for some embodiments, the first link 122 comprises an L-shape. In some embodiments the first link 122 is configured to have a recess formed therein for receiving the second link 124 and to permit the second link 124 to rotate relative to the first link 122.

The proximal end of the second link 124 is connected to the distal end of the third link 126 by the third joint 132. The third joint 132 can be configured to allow the handle 104, the first link 122, and the second link 124 to rotate relative to the third link 126. In the illustrated embodiment, the third joint 132 allows the handle 104, the first link 122, and the second link 124 to rotate around a pitch axis 139. In some embodiments, the pitch axis 139 extends through the third joint 132 and intersects with the roll axis 136 and the yaw axis 138 at the center point of the handle 104. The third joint 132 can be a revolute joint. As shown, for some embodiments, the second link 124 comprises an L-shape. In some embodiments, the L-shaped second link 124 is received in a recess of the L-shaped first link 122 (as shown in FIG. 17). In other embodiments, the L-shaped first link 122 can be received in a recess of the L-shaped second link 124.

In the illustrated embodiment, the first joint 128, the first link 122, the second joint 130, the second link 124, and the third joint 132 provide three rotational degrees of freedom allowing the rotation of the handle 104 to be adjusted in pitch, roll, and yaw. In the illustrated embodiment, the gimbal 106 further includes a third link 126 and fourth joint 134 providing a redundant rotational degree of freedom. This need not be included in all embodiments, but can provide greater mechanical flexibility for the gimbal 106.

As shown, the distal end of the third link 126 is connected to the proximal end of the second link 124 by the third joint 132. The proximal end of the third link 126 is connected to the distal end of the positioning platform 108 by the fourth joint 134. The fourth joint 134 can be configured to allow the handle 104, the first link 122, the second link 124, and the third link 126 to rotate relative to the positioning platform 108. In the illustrated embodiment, the fourth joint 134 allows the handle 104, the first link 122, the second link 124, and the third link 126 to rotate around an axis 141. In some embodiments, the axis 141 is parallel to the yaw axis 138. In some embodiments, the yaw axis 138 and the axis 141 are coaxial, although, as illustrated, this need not be the case in all embodiments. The axis 141 (and the yaw axis 138) can be parallel to the direction of gravity to maintain the orientation of the gimbal relative to the direction of gravity as described above. The fourth joint 134 can be a revolute joint. As shown, for some embodiments, the third link 126 comprises an L-shape.

A haptic interface device (HID) is a device that provides haptic feedback, and includes any of the controllers described herein for controlling a robotic system, robotic arm, and/or instrument. In some embodiments, input sensors are distinct from the haptic interface device. In some embodiments, the HID includes a haptic feedback device and an input device (e.g., a grasper, such as handle 104) that is configured to be held by the operator. In some embodiments, HID includes components that are designed or selected to have minimal mechanical dissipative effects such as friction and damping. In this manner, the HID is designed to be transparent to the user/operator, so that the user does not feel much resistance or impedance when moving the HID in free space, allowing the user to complete a surgical task with minimum burden and distraction imposed by the HID.

Figure 23:
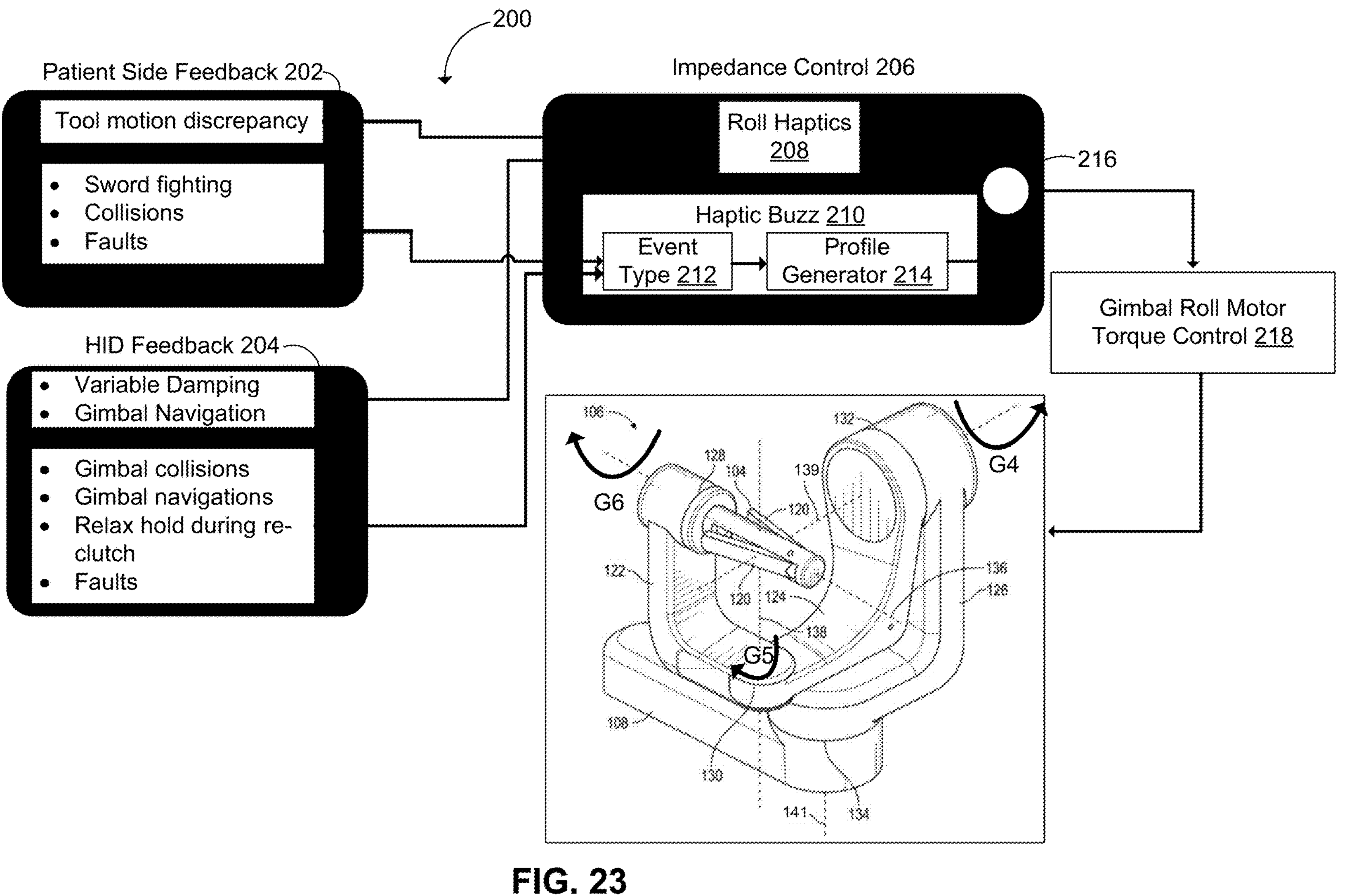
FIG. 23 depicts a control system 200 in accordance with some embodiments.

FIG. 23 depicts a control system 200 for providing haptic feedback to an operator, in accordance with some embodiments. The control system 200 receives patient side feedback 202, from operations and/or statuses of one or more robotic arms 12, and HID feedback 204, from operations and/or statuses of one or more input devices (e.g., controller 302). Both the patient side feedback 202 and the HID feedback 204 are provided to an impedance control unit 206. In some embodiments, the patient side feedback 202 includes information indicating events, states, or operations associated at least in part with the medical instrument 310 (e.g., tool motion discrepancy, collision between two medical instruments as called "sword fighting," collisions between robotic arms, collisions between a robotic arm and a surrounding, such as collisions between the robotic arm and a static component in an operating room, faults, etc.). In some embodiments, the HID feedback 204 include information indicating events, states, or operations associated with the one or more input devices (e.g., controller(s) 302), such as variable damping, gimbal navigation, gimbal collisions, relax hold during re-clutch, faults, etc. In some embodiments, the patient side feedback 202 and/or the HID feedback 204 is generated (or provided or updated) based on an input signal from one or more input sensors (e.g., sensors, such as encoders, coupled with the one or more input devices, such as controller 302 In some embodiments, the impedance control unit 206 includes two modules: a roll haptics module 208 and a haptic buzz module 210. In some embodiments, the haptic buzz module 210 further includes two components, an event type classifier 212 and a profile generator 214.

In some embodiments, outputs from both the roll haptics module 208 and the haptic buzz module 210 are combined at a signal controller 216 (also called a signal combiner), and delivered to the HID. In some embodiments, the output from the haptics buzz module 210 includes a vibrational tactile feedback signal. In some embodiments, the output from the roll haptics module 208 includes a kinesthetic haptic feedback signal. For example, an output control signal from the signal controller 216 is provided to a component (e.g., an actuator or a controller therefor) of the HID. In some embodiments, the component is a torque/current control loop 218 of the HID, and the HID includes a gimbal 106. In some embodiments, the torque/current control loop 218 controls a motor of gimbal 106. In some embodiments, the motor is a gimbal roll motor of the gimbal 106.

In some embodiments, the patient side feedback 202 is generated (or provided or updated) when an event of a first set of predefined events (e.g., a tool motion discrepancy) is detected by (or based on) one or more input sensors (e.g., the patient side feedback 202 includes information indicating an event of the first set of predefined events, for providing a kinesthetic haptic feedback). Tool motion discrepancies occur when a master command signal (e.g., a control signal) received by a robotic arm 12 results in an output motion of the robotic arm 12 (or a coupled surgical tool) that deviates from a desired motion that corresponds to the master command signal (e.g., the robotic arm 12 moves more than specified by the master command/control signal, the robotic arm 12 moves less than specified by the control signal, the robotic arm 12 moves at a speed less than specified by the control signal by a predefined threshold, the robotic arm 12 moves in a different direction than specified by the control signal, etc.). In some embodiments, the tool motion discrepancy is detected when a processor of the robotic system 10 determines based on one or more input sensors (e.g., encoders at or near one or more motors of the robotic arm 12, one or more inertia sensor(s), etc.) in the robotic arm 12 that a current position of the robotic arm deviates from a predicted position based on a control signal sent to the robotic arm 12. In accordance with the processor detecting or determining an event of the first set of predefined events (e.g., a tool motion discrepancy), an output signal is sent as a patient side feedback 202 to the roll haptics module 208 of the impedance control unit 206. In some embodiments, the patient side feedback 202 causes a kinesthetic haptic feedback to be produced.

In some embodiments, the patient side feedback 202 is generated (or provided or updated) when an event of a second set of predefined events (e.g., "sword fighting" is about to occur, or has occurred) is detected by (or based on) one or more input signals (e.g., the patient side feedback 202 includes information indicating an event of the second set of predefined events, for providing a vibrational tactile feedback). In some embodiments, the second set of predefined events is mutually exclusive to the first set of predefined events. Instrument "sword fighting" occurs when an instrument shaft is within or less than a threshold distance (e.g., less than 10 cm, less than 5 cm, less than 2 cm, or less than 1 cm) to a different instrument shaft or a collision has occurred between two instrument shafts. In some embodiments, the instrument shaft is a portion of a medical instrument that is directly or indirectly grasped, mechanically, by the robotic arm 12 (e.g., via instrument drivers 28.) For example, an instrument shaft of a first medical instrument held and controlled by a first robotic arm may be within or less than the threshold distance to an instrument shaft of a second medical instrument held and controlled by a second robotic arm. In some embodiments, instrument "sword fighting" is detected when a processor of the robotic system 10 determines based on one or more sensors (e.g., encoders at or near one or more motors of the robotic arm, one or more inertia sensor(s)) in the first and second robotic arms and dimensions of the first and second medical instruments that a current position of the first medical instrument handled (or held) by the first robotic arm is within the threshold distance form a current position of the second medical instrument handled (or held) by the second robotic arm. When the processor detects instrument "sword fighting," an output signal is sent as a patient side feedback 202 to the haptics buzz module 210 of the impedance control unit 206. The patient side feedback 202 causes a vibrational tactile haptic feedback to be produced. In some embodiments, haptics technologies relying on tactile stimulations transmit a mechanical stimulus to the skin of the operator. The mechanical stimulus includes vibrational stimulus, surface change stimulus, or frictional change stimulus. In some embodiments, tactile feedback generates sensations such as vibration, friction, or micro-deformation.

In some embodiments, robotic arm "sword fighting" is deemed to have occurred when a first robotic arm is within or less than a threshold distance (e.g., less than 10 cm, less than 5 cm, less than 2 cm, or less than 1 cm) to a different robotic arm or a collision has occurred between two robotic arms. In some embodiments, "sword fighting" is deemed to have occurred when a medical instrument held by a first robotic arm is within or less than the threshold distance (e.g., less than 10 cm, less than 5 cm, less than 2 cm, or less than 1 cm) to a different robotic arm or a collision has occurred between the medical instrument and a robotic arm.

In some embodiments, the patient side feedback 202 includes information indicating an event of an instrument shaft of the first medical instrument and/or a robotic arm coming into a proximity to, or colliding with, a camera in a patient-body workspace (for monitoring a portion of a patient-body workspace). The information may be used for providing a vibrational tactile feedback. In some embodiments, the patient-body workspace is a space within the patient. Collision or near collision between an instrument arm and the camera occurs when an instrument shaft and/or a robotic arm is within a threshold distance (e.g., less than 10 cm, less than 5 cm, less than 2 cm, or less than 1 cm) to a camera or a collision has occurred between the camera and the instrument shaft and/or the robotic arm.

In some embodiments, the collision (or impending collision) is detected by a processor of the robotic system 10 based on one or more input sensors (e.g., encoders at or near one or more motors of the robotic arm, one or more inertia sensor(s)) in the robotic arm in accordance with a determination that a current position of the robotic arm and/or an instrument handled by the robotic arm is less than the threshold distance from the camera. In accordance with the processor detecting a collision or a near collision, an output signal is sent as a patient side feedback 202 to the haptics buzz module 210 of the impedance control unit 206.

In some embodiments, the patient side feedback 202 includes information indicating a fault condition (e.g., at least one of fault conditions is detected) (e.g., for providing a vibrational tactile feedback). Examples of fault conditions associated with the patient side feedback 202 include detecting an excessive force (e.g., a force above a force threshold) on a robotic arm (e.g., caused by a collision between a robotic arm and an environment, such as a patient, a nurse, etc.).

In some embodiments, HID feedback 204 includes information indicating a level of variable damping provided by the HID during navigation of the gimbal 106. For example, based in part on how the HID is manipulated by the user, appropriate levels of varying damping resistance are applied to the HID generally, or one or more joints (e.g., joints 128, 130, 132, and 134) of the HID to modify force(s) or torque(s) provided by the one or more joints. The variable damping (or a change thereto) may be used to provide a kinesthetic haptic feedback. For example, an increase in the level of damping can indicate is provided as an input signal (e.g., HID feedback 204) to the roll haptics module 208 of the impedance control unit 206. In some embodiments, the impedance control unit 206 changes the level of damping from the current level of variable damping as indicated by the HID feedback 204 provided to the impedance control unit 206 when the tool motion discrepancy is determined based on information in the patient side feedback 202, to provide, or alter, a kinesthetic haptic feedback.

In some embodiments, the HID feedback 204 includes information indicating a first gimbal coming into a proximity to, or colliding with, a second gimbal (e.g., left gimbal of FIG. 19 colliding with right gimbal of FIG. 19) (e.g., for providing a vibrational tactile feedback). Collision or near collision between the first gimbal and the second gimbal occurs when the two gimbals are within or less than the first threshold distance (e.g., less than 20 cm, 10 cm, less than 5 cm, less than 2 cm, or a collision has occurred) apart. In some embodiments, a collision between two gimbals is detected when a processor of the robotic system 10 determines based on sensors (e.g., encoders at or near one or more motors of the gimbals, one or more inertia sensor(s)) in the first and second gimbals that a current position of the first gimbal is within the first threshold distance form a current position of the second gimbal.

In some embodiments, the HID feedback 204 includes information indicating navigation (e.g., movement) of a gimble (e.g., position and/or speed), which may be compared with the movement of the medical instrument 310 for determining whether the tool motion discrepancy has occurred or whether the tool motion discrepancy has exceeded a predefined threshold (e.g., for providing a kinesthetic haptic feedback). For example, when the gimbal is near an end of a travel range for a particular degree freedom, HID feedback 204 indicating the gimbal position or the gimbal's proximity to the end of the travel range is provided to the to the roll haptics module 208 of the impedance control unit 206 for providing a kinesthetic haptic feedback (e.g., increased damping). In some embodiments, when the gimbal exceeds a velocity threshold during navigation, HID feedback 204 including information indicating the speed of the gimbal or information indicating that the gimbal has exceeded the velocity or speed threshold is provided to the roll haptics module 208 of the impedance control unit 206 for providing a kinesthetic haptic feedback.

In some embodiments, the information indicating the navigation of the gimbal may be used for providing a vibrational tactile feedback. For example, when the gimbal reaches the end of a travel range for a particular degree freedom, HID feedback 204 indicating the gimbal reaching the end of the travel range is provided to the to the haptic buzz module 210 of the impedance control unit 206 for providing a vibrational tactile feedback.

In some embodiments, the HID feedback 204 includes information indicating whether a user needs to relax her hold on the HID. For example, when a user has over-articulated the gimbal, beyond a particular threshold (e.g., after hitting a haptic boundary), the HID feedback 204 may include information indicating whether the user needs to relax her hold on the HID. When the processor detects indicating whether a user needs to relax her hold on the HID, an output signal is sent from the HID feedback 204 to the haptics buzz module 210 of the impedance control unit 206. The HID feedback 204 causes a vibrational tactile haptic feedback to be produced. The vibrational tactile feedback provided in response to the information indicating whether a user needs to relax her hold on the HID informs the user that the gimbal has moved beyond a tool reach. In some cases, once the user's hold on the HID is relaxed, the system may reorient the gimbal (automatically) to match the tool pose. In some other cases, a user may need to reorient his or her hand position during a procedure, and pressing on the clutch button can temporarily decouple the HID from controlling operation of the instruments, thereby allowing the user to reorient his or her hand position to regrip the HID during a procedure. When a user relaxes her hold, such a gesture may be interpreted by HID or the robotic system as returning to the clutch state (e.g., re-engaging the "clutch").

In some embodiments, the HID feedback 204 is generated when fault conditions are detected. Examples of fault conditions associated with the HID feedback 204 include detecting a collision of a gimbal (e.g., with an arm rest or with the other gimbal) or determining that a redundant joint is unable to move (due to a collision).

In some embodiments, when the haptic buzz module 210 receives signals from the patient side feedback 202, a first type of tactile output is generated, and when signals are received from the HID feedback 204, a second type of tactile output is generated. In some embodiments, the first type of tactile output is distinct from the second type of tactile output. In some embodiments, the first type of tactile output has a first vibrational frequency component (e.g., a frequency between 10 and 20 Hz) and the second type of tactile output has a second vibrational frequency component (e.g., a frequency between 50 and 100 Hz, or between 100 Hz to 200 Hz, etc.) that is distinct from the first vibrational frequency component. In some embodiments, the first type of tactile output has a first vibrational pattern (e.g., saw-tooth pattern) and the second type of tactile output has a second vibrational pattern (e.g., square-wave pattern) that is distinct from the first vibrational pattern. In some embodiments, the first type of tactile output has a first duration (e.g., 0.4 seconds, 0.5 seconds, 0.6 seconds, 0.7 seconds, 0.8 seconds, 0.9 seconds, 1 second, or semi-continuous) and the second type of tactile output has a second duration that is distinct from the first duration (e.g., 0.1 seconds, 0.2 seconds, 0.3 seconds, etc.). In some embodiments, the first type of tactile output has a first number of chirps (3 chirps) and the second type of tactile output has a second number of chirps that is distinct from the first number of chirps (e.g., 5 chirps). A user may be able to more intuitively disambiguate between the two types of tactile outputs and more quickly recognize an issue that has arisen either on the patient side or on the HID side.

When system is operating, various feedback received from the patient side or the HID side may create certain events that in return trigger either or both traditional haptic and buzz effect feedbacks.

In some embodiments, the impedance control unit 206 is implemented as one or more processors (e.g., microprocessors, application specific integrated circuit, etc.). For example, both the roll haptics module 208 and the haptic buzz module 210 may be implemented in a single processor or two separate processors. In some embodiments, the gimbal roll motor torque control 218 is implemented in the same processor as the impedance control unit 206 or in a separate processor. In some embodiments, the robotic system 10 includes one or more processors for processing the patient side feedback 202 and/or the HID feedback 204. In some embodiments, the circuit for processing the patient side feedback 202 and/or the HID feedback 204 is included in the one or more processors implementing the impedance control unit 206.

i. Roll Haptics Module

In some embodiments, the roll haptics module 208 applies a damping function to a robotic joint (e.g., the robotic joint 24) to modify a resistance to motion of the robotic joint (e.g., the damping function causes, by application of a damping coefficient, an increase in resistive force or torque to motion of the robotic joint. In some embodiments, a joint velocity is received or determined, and the damping function applied to the robotic joint may also be based on the current velocity. In some embodiments, as a medical tool handled by the robotic joint is moved within a three-dimensional space, a current position and/or a current velocity of the robotic joint is received or determined (e.g., by a control unit, by the impedance control 206). In some embodiments, each joint 24 reports its speed and position (e.g., angular speed and angular position) to the control unit. Additionally or in the alternative, a joint 24 may report an angular force or torque imparted by or applied to the joint.

In some embodiments, the control unit (e.g., the impedance control 206) then determines a distance (e.g., a rotational distance of the joint) between the current position of the robotic joint 24 (e.g., a rotational position of the robotic joint 24) and a first motion limit of the robotic joint. In some embodiments, the roll haptics module 208 implements kinesthetic haptics technologies, which involve exercising a force on the user that impedes a limb movement. Kinesthetic haptics feedback is usually not felt on the skin, but mainly on the muscles and tendons. In some embodiments, the kinesthetic haptic feedback includes a continuous force applied against a user input. In some embodiments, kinesthetic haptics feedback involves the perception of body movements, and the ability to detect changes in body position and movements without relying on information from the five senses. In some embodiments, kinesthetic haptics feedback mimics the real behavior of a robotic arm.

The roll haptics module 208 provides, as its output, an output control signal that is used to generate a kinesthetic haptic feedback at the HID.

ii. Haptic Buzz Module

The haptic buzz module 210 receives input signs from the patient side feedback 202 and/or the HID feedback 204. The input signal is sent to an event type classifier 212 in the haptic buzz 210. In some embodiments, the event type classifier 212 identifies the source of the received signal (e.g., from the patient side feedback 202 or from the HID feedback 204), and the condition conveyed by the received signal (e.g., gimbal collisions, faults, sword fighting, etc.), and provides an output signal to the profile generator 214. In some embodiments, the output signal is unique to each type of event or information. The profile generator 214 provides an output control signal corresponding to the identified type of event indicated in the output signal (e.g., the profile generator 214 may provide a unique output control signal for each identified type of event so that the HID may provide a unique haptic or tactile feedback indicating the identified type of event). The output control signal is used to generate a tactile signal at the HID. In some embodiments, a user can determine the type or profile of the tactile signal to be associated with each event types (e.g., faults from the HID feedback 2014, faults from patient side feedback 202, gimbal collisions, sword fighting, medical instrument collisions, camera collisions, relax hold during re-clutch, etc.). In some embodiments, the profile generator 214 automatically generates and assigns a tactile signal for one or more of the event types.

A signal controller 216 generates a combined signal from the output control signal of the roll haptics module 208 and the output control signal of the haptic buzz module 210. In some embodiments, the signal controller 216 adds the output control signal from the roll haptics module 208 and the output control signal from the haptic buzz module 210. In some embodiments, the signal controller 216 adds a first weighted amount of the output control signal (e.g., a fraction of the output control signal, multiples of the output control signal) from the roll haptics module 208 and a second weighted amount of the output control signal from the haptic buzz module 210 to generate a final output control signal used to control a portion of a robotic joint. In some embodiments, the portion of the robotic joint corresponds to a gimbal roll motor, and the final output signal is delivered to the torque control loop 218 of the gimbal roll motor for torque control.

Figure 24:
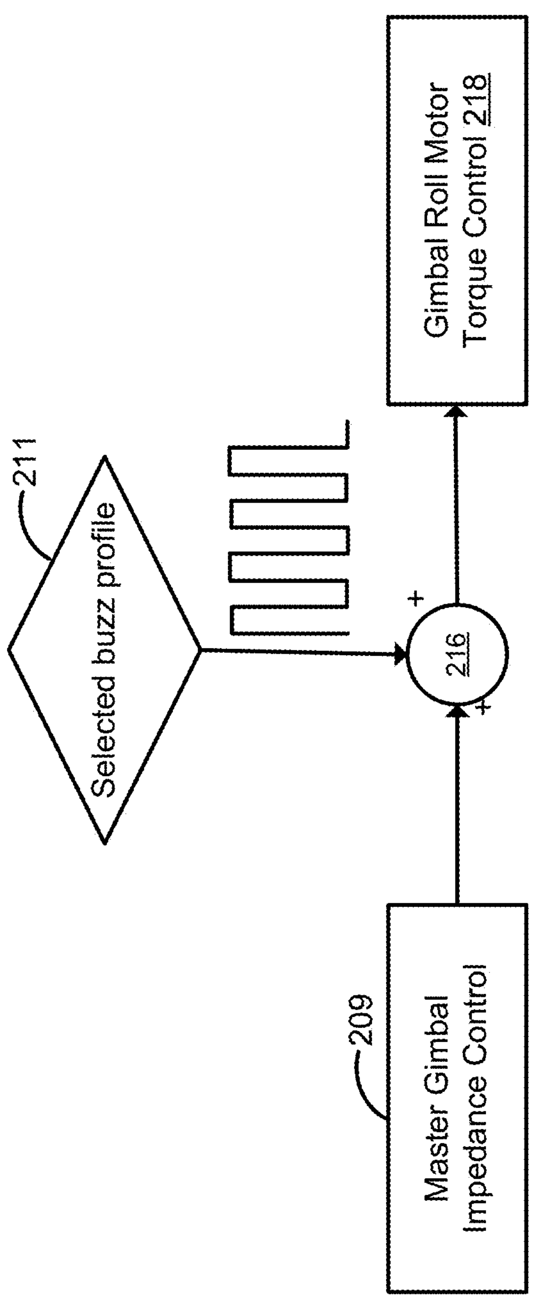
FIG. 24 shows how output signals are combined, in accordance with some embodiments.

FIG. 24 shows how output signals from the roll haptics module 208 and the haptic buzz module 210 are combined, in accordance with some embodiments. A master gimbal impedance control 209, which represents the output from the roll haptics module 208 is provided to the signal controller 216. In some embodiments, the master gimbal impedance control 209 is a non-periodic signal. A selected buzz profile 211, which represents the output signal from the buzz haptics module 210 is also provided to the signal controller 216. In some embodiments, the selected buzz profile 211 is a periodic signal. In some embodiments, the selected buzz profile 211 is used to generate physical vibrations (e.g., periodic physical vibrations, such as alternating between a high frequency vibration and a low frequency vibration or alternating between a state of providing vibration and a state of providing no vibration). In some embodiments, a frequency of the physical vibrations is at least 10 Hz (e.g., at least 50 Hz, or between 50 Hz and 200 Hz). In some embodiments, the frequency is between 4-10 Hz, or around 6 Hz. The frequency profile of the vibration causes the buzz effect to be easily identifiable by the user, allowing information (indicating an associated event) to be communicated in a distinct and identifiable way to the user. Frequency of the physical vibrations is selected to be far away from normal teleoperation master control (e.g., 5 Hz or less) and roll haptic (e.g., kinesthetic haptic) feedback, so this vibration only provides a vibrational tactile haptic effect and does not affect an existing operation. The waveform, amplitude, frequency, duration, repeating pattern, etc., can be selected further based on hardware modal analysis (e.g., the hardware modal analysis may include determination of different modes of the vibration on the hardware and preventing or avoiding the use of excitation frequencies associated with such modes to avoid or reduce resonances) and various needs associated with haptic presentation for different applications.

In some embodiments, the buzz haptic or vibrational tactile feedback has varying amplitudes (e.g., an alternating high and low amplitude variation for events, such as collisions or faults, and a monotonically increasing or decreasing amplitude variation for events derived for too motion discrepancy). In some embodiments, the signal controller 216 determines a weighted sum of the control signal from the master gimbal impedance control 209 and the output control signal from the selected buzz profile 211 (e.g., by adding a first weighted value corresponding to the control signal from the master gimbal impedance control 209 (e.g., a fraction of the output control signal or a multiple of the output control signal) and a second weighted value corresponding to the output control signal from the selected buzz profile 211) to generate a final output control signal used to control a portion of a robotic joint. In some embodiments, the portion of the robotic joint corresponds to a gimbal roll motor, and the final output signal is delivered to a torque control loop 218 for torque control of the gimbal roll motor.

Returning to FIG. 23, in some embodiments, the positioning platform 108 of the robotic system 10 includes a gimbal 106 at its distal end. The gimbal 106 further includes a number of motors. In some embodiments, the motor adjacent to the handle 104 (e.g., at a most distal end of the gimbal 106) (e.g., G6) receives a superimposed vibrational tactile control signal into its torque/current control loop, in addition to the kinesthetic haptic signal from the master gimbal impedance control, to generate buzzing vibration on top of the kinesthetic/roll haptic signal. The G6 motor may provide a torque (e.g., rotational resistance) to the handle 104 (and the first joint 128) about the roll axis 136. In some embodiments, the roll axis 136 is aligned with a longitudinal axis of the handle 104. In some embodiments, providing the vibrational tactile signal at the most distal end of the gimbal 106 facilitates the user to sense the vibrational tactile signal. In some embodiments, the roll haptics signal causes the user to experience a resistance (e.g., a kinesthetic haptic feedback) when the user applies a torque to the handle 104 about the roll axis 136. The gimbal includes other motors, for example, a motor G5 that provides a torque about a yaw axis 138, and a motor G4 that provides a torque about a pitch axis 139.

Various buzz profiles can be used to warn a user of different events, such as an imminent physical collision between the gimbals, between a gimbal and a positioning platform arm (e.g., the positioning platform 108 of a first gimbal colliding with a second gimbal), between medical instruments, or between robotic arms. A vibrational buzz profile can also be used to warn the user of an imminent physical collision between a gimbal and a console workspace boundary (including other components of the robotic system 10, such as a display, or any other objects adjacent to the gimbal) (e.g., between the console 16 and the gimbal 106).

In some embodiments, the medical system includes a second haptic interface device that is distinct from the first haptic interface device (e.g., FIG. 19 shows two haptic interface devices).

3. Variable Damping for Haptic Interface Control

In some embodiments, the kinesthetic haptic feedback includes application of a torque (or a force) by an actuator (e.g., a motor) to provide a resistance to a user input. In some embodiments, roll haptics associated with the HID involves application of variable damping during navigation and/or operation of the HID. In some embodiments, a difference in position between master and slave is determined so as to provide feedback forces to the operator.

A variable damping method provides appropriate levels of damping resistance to the system and/or user based in part on how the HID is manipulated by the user. A damping algorithm may employ a damping function with multiple damping regimes. As an example, one damping regime may provide a relatively low amount of resistance to a user (e.g., similar to a hand running through water), while a different damping regime may provide a relatively higher amount of resistance to a user (e.g., think of a hand running through molasses). Another damping regime may provide a variable amount of resistance depending on the motion information received from the gimbal (e.g., from the joint(s)). In some embodiments, the resistance may be proportional or inversely proportional to motion information from the medical instrument and/or the gimbal.

Incorporation of multiple or variable damping regimes may be used to provide a kinesthetic haptic feedback. For example, providing a low damping coefficient may indicate to a surgeon that there are no issues with the surgeon's movement of the gimbal, whereas providing a high damping coefficient may indicate to the surgeon that there may be issues (e.g., in proximity to an end of a travel range). Increasing the damping coefficient may indicate that a heightened level of attention may be required (e.g., moving toward the end of the travel range) and decreasing the damping coefficient may indicate that a lower level of attention may be required (e.g., moving away from the end of the travel range).

Figure 25A:
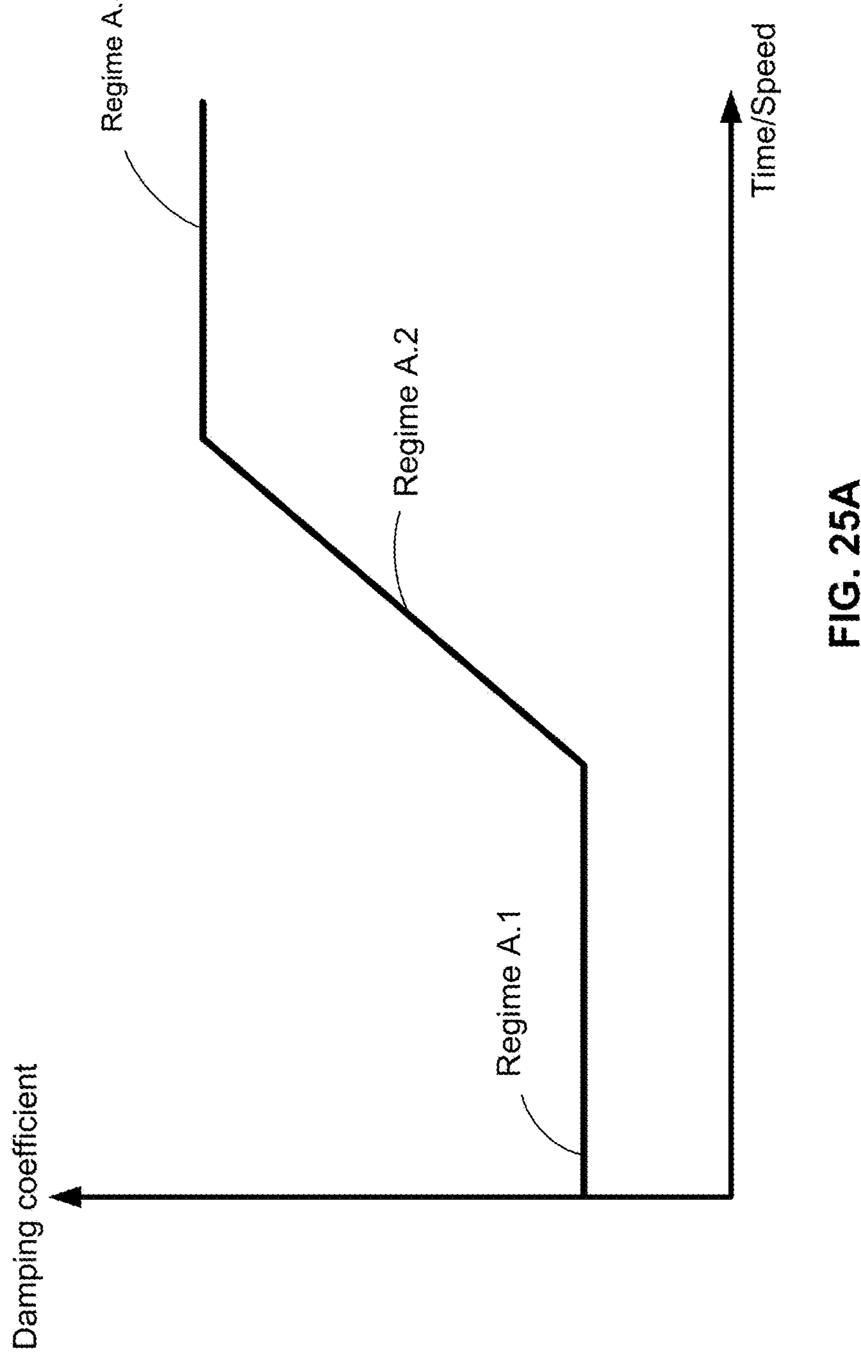
FIG. 25A depicts an example damping function having different damping coefficients, in accordance with some embodiments.

FIG. 25A depicts an example of a damping function used in master gimbal impedance control 209 in the roll haptics module 208, in accordance with some embodiments. In some embodiments, a low damping coefficient is desired (Regime A.1) while a high damping coefficient is desirable, for example to provide a warning (Regime A.3). To avoid or minimize a sudden jump between the low damping regime (Regime A.1) and the high damping regime (Regime A.3), a transition damping region (Regime A.2) bridges Regime A.1 and Regime A.3.

The applied damping coefficient(s) may be selected to modify a force or torque provided by one or more robotic joints to provide a resistance to the user input. The force or torque may be, for example, modified by a fixed amount when a current speed or velocity of a portion of the robotic user interface is within a first range (corresponding to, e.g., Regime A.1), by a variable amount (e.g., increasing in the depicted implementation) when a current speed or velocity of a portion of the robotic user interface is within a second range (corresponding to, e.g., Regime A.2), and by another fixed amount when the current speed or velocity is within a second range greater than the first range (corresponding to, e.g., the depicted plateau of Regime A.3).

While the depicted damping region provides for a continuous transition, in some embodiments the transition may not be continuous. For example, the transition may include several subregions, each with its own damping coefficient that is distinct from the damping coefficients of other subregions, ultimately progressing to the high damping region.

Figure 25B:
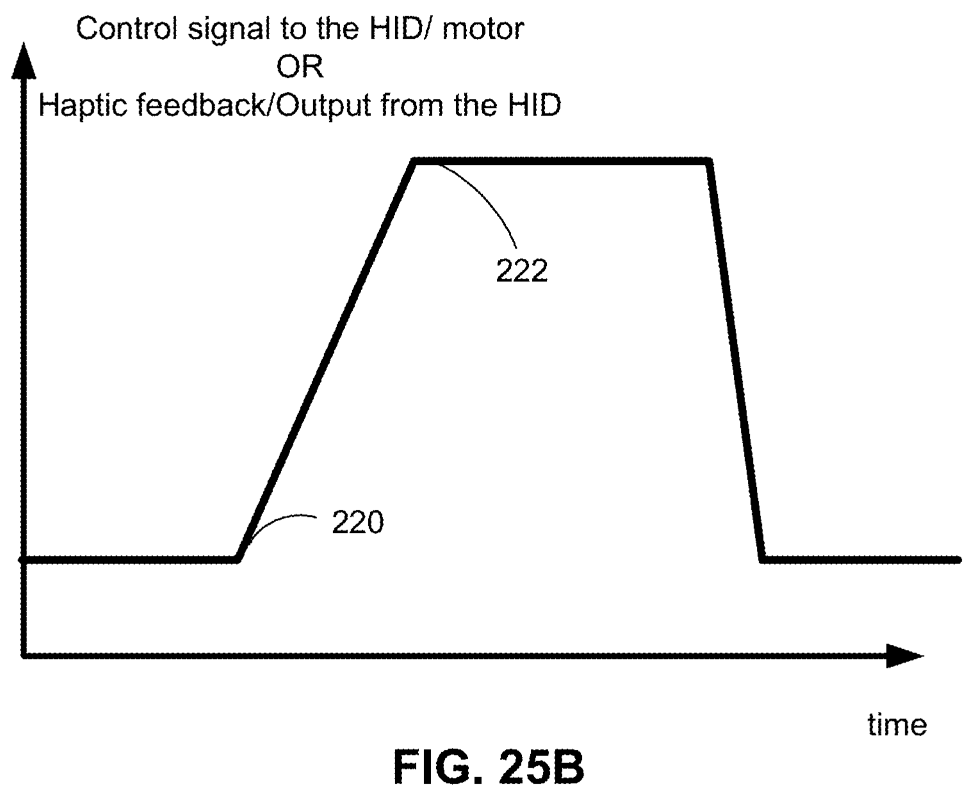
FIG. 25B depicts an example control signal to a haptic interface device (HID) or an output response from the HID, in accordance with some embodiments.

FIG. 25B depicts an example of a portion of the output signal (e.g., a voltage or a current) that is provided to the HID (for generating a haptic and/or tactile feedback), in accordance with some embodiments. In some embodiments, at least a portion of the output signal from the signal controller 216 derived from the master gimbal impedance control 209 is provided to a torque/current control loop of a component of the HID. In some embodiments, the component of the HID is a gimbal roll motor (e.g., G6) of the HID. FIG. 25B shows a control signal (e.g., a current) provided to the HID as a function of time, that is derived from the master gimbal impedance control 209, for providing kinesthetic haptic feedback. The same plot also depicts a haptic feedback or output (e.g., a force) from the HID that is experienced by the user. In some embodiments, the haptic feedback is a kinesthetic feedback. In some embodiments, the kinesthetic haptic feedback is provided for a duration of at least 0.5 seconds.

As a user begins interacting with the HID, a constant control signal may be sent to the HID to provide a fixed amount of resistance, as kinesthetic feedback against the user's movement of the HID. At a time 220, one or more signals are received as part of the HID feedback 204 and/or patient side feedback 202, and the roll haptics module 208 causes a variable damping signal for increasing the resistance provided by the HID. For example, tool motion discrepancy causes the patient side feedback 202 to be sent to the impedance control 206, and/or gimbal navigation causes HID feedback 204 to be sent to the impedance control 206. An example of gimbal navigation that causes a signal from the HID feedback 204 to be sent is a gimbal being navigated toward an end of travel range of the gimbal. In some embodiments, at a time 222, the gimbal is near the end of its travel range, and a large damping coefficient is applied to make it more difficult to move the HID to the end of its travel range. The control signal is decreased (to reduce an amount of damping) when the HID moves away from the end of its travel range.

Figure 25C:
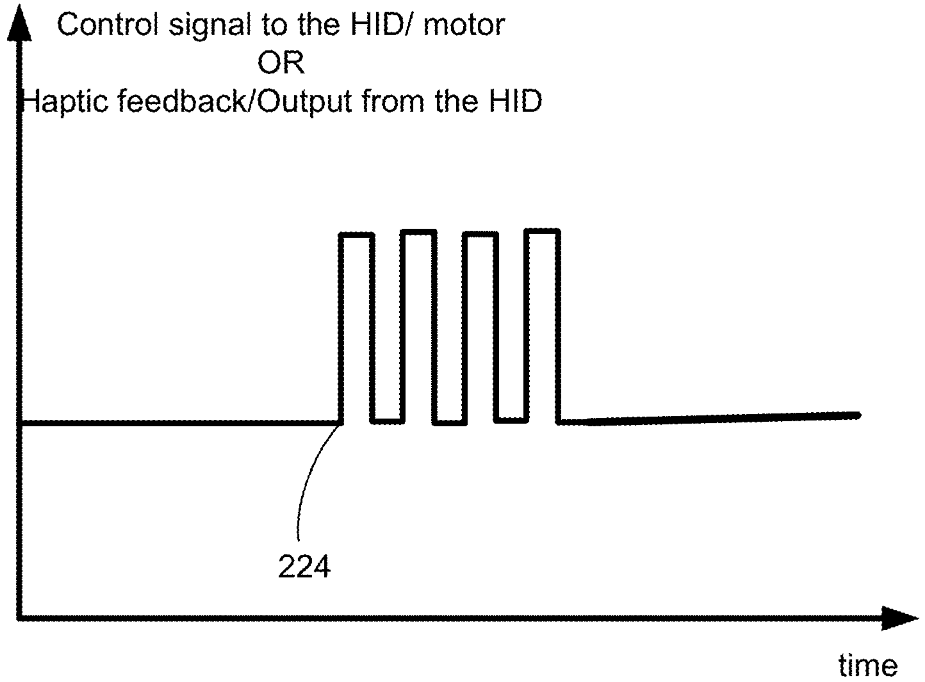
FIG. 25C depicts an example control signal to the HID or an output response from the HID, in accordance with some embodiments.

FIG. 25C shows a control signal (e.g., a voltage or a current) provided to the HID as a function of time, that is derived from the haptic buzz module 210, for providing vibrational tactile haptic feedback to the user. At a time 224, one or more signals are received from the HID feedback 204 and/or patient side feedback 202, and the haptic buzz module 210 causes physical vibrations to be generated at the HID. The physical vibrations are at least 50 Hz, or may be between 50 Hz and 200 Hz. The high-frequency profile of the vibration causes the buzz effect to be easily identifiable by the user, allowing information to be communicated in a distinct and identifiable way to the user (as compared to the low frequency kinesthetic feedback). For example, one or more of: sword fighting, collisions, /or other faults cause the patient side feedback 202 to be sent to the impedance control 206 for providing a vibrational feedback. Additionally, or alternatively, one or more of: gimbal collision, gimbal navigations, faults, or relax of hold during re-clutch cause HID feedback 204 to be sent to the impedance control 206 for providing a vibrational feedback. An example of gimbal navigation that causes a signal from the HID feedback 204 to be sent for providing a vibrational feedback is a movement of a gimbal that lead to an imminent collision with a second gimbal.

Figure 25D:
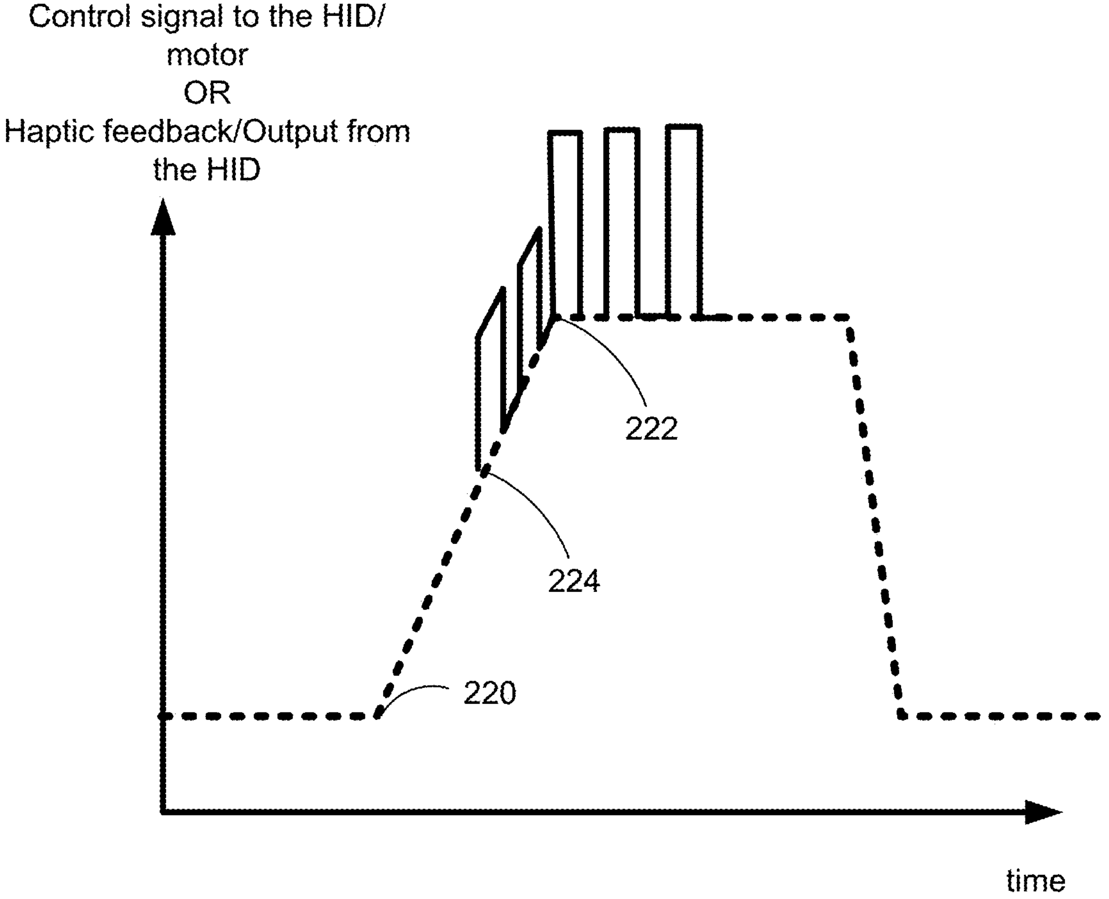
FIG. 25D depicts an example control signal that is a combination of the control signals shown in FIGS. 25B and 25C, in accordance with some embodiments.

FIG. 25D shows a control signal (e.g., a voltage or a current) provided to the HID from the signal controller 216 that combines the control signals from both the roll haptics module 208 and the haptic buzz module 210. In some embodiments, the control signal provided from the signal controller 216 is a sum (or a weighted sum) of the signal shown in FIG. 25B and the signal shown in FIG. 25C. Due to the different characteristics of the kinesthetic haptic feedback and the vibrational tactile haptic feedback, a user can identify at time 220, time 224, and time 222, feedback from the HID that indicates various events associated with the medical instrument and/or the gimbal.

Figure 26:
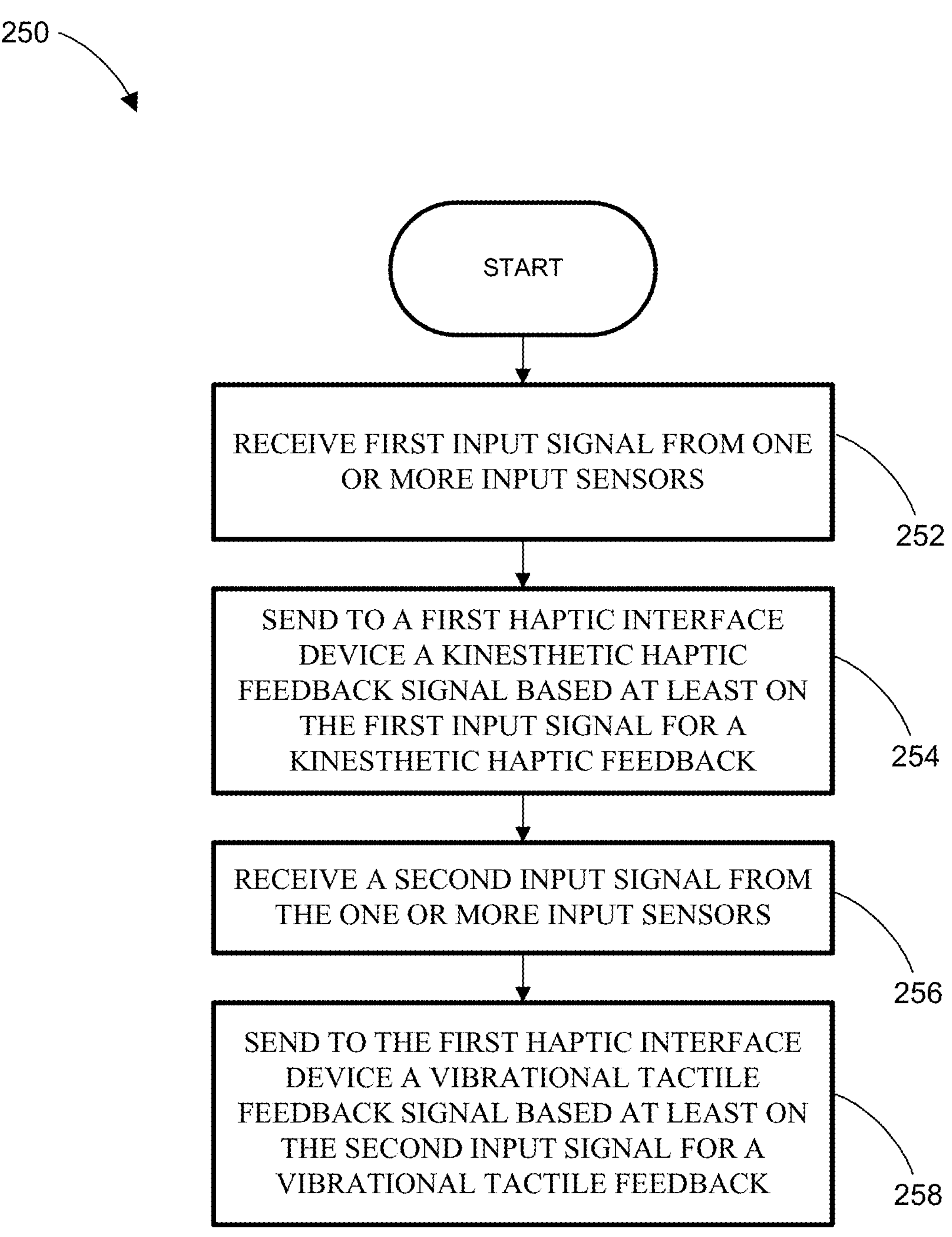
FIG. 26 is a flow chart illustrating an embodiment of a method for providing feedback to a user.

FIG. 26 is a flow chart illustrating an example method 250 in which a haptic feedback device provides feedback to the user while the user uses a controller (e.g., a master) to control a medical instrument (e.g., a slave). The method 250 can be configured for hybrid control, using both impedance and admittance control. Although illustrated sequentially, the blocks of the method 250 can be implanted in other orders or one or more of the blocks can occur at substantially the same time. The method 250 begins at block 252, where the system receives a first input signal from one or more input sensors. At block 254, the system sends to a first haptic interface device a signal of a first type (e.g., a kinesthetic haptic feedback signal) based at least on the first input signal for (e.g., providing or generating) a feedback of a first type (e.g., a kinesthetic haptic feedback).

At block 256, the system receives a second input signal from the one or more input sensors. At block 258, the system sends to the first haptic interface device a signal of a second type (e.g., a vibrational tactile feedback signal) based at least on the second input signal for (e.g., providing or generating) a feedback of a second type (e.g., a vibrational tactile feedback).

4. Implementing Systems and Terminology

Implementations disclosed herein provide systems, methods and apparatus for robotically enabled medical systems. Various implementations described herein include controllers for the robotically enabled medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" or "about" refers to a range of measurements of a length, thickness, a quantity, time period, or other measurable value. Such range of measurements encompasses variations of +/−10% or less, preferably +1-5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

5. Illustration of Subject Technology as Clauses

Some embodiments or implementations are described with respect to the following clauses:

Clause 1. A medical system, comprising:

a first haptic interface device;

one or more input sensors;

one or more processors; and memory storing instructions, which, when executed by the one or more processors, cause the one or more processors to:

receive a first input signal from the one or more input sensors;

send to the first haptic interface device a kinesthetic haptic feedback signal based at least on the first input signal for a kinesthetic haptic feedback;

receive a second input signal from the one or more input sensors; and send to the first haptic interface device a vibrational tactile feedback signal based at least on the second input signal for a vibrational tactile feedback.

Clause 2. The medical system of Clause 1, further comprising a first robotic arm.

Clause 3. The medical system of Clause 2, wherein the first input signal is based on a difference between a master command and a movement of the first robotic arm.

Clause 4. The medical system of Clause 2 or Clause 3, further comprising a second robotic arm that is distinct from the first robotic arm.

Clause 5. The medical system of Clause 4, wherein the second input signal is derived from a collision between the first robotic arm and the second robotic arm.

Clause 6. The medical system of Clause 4 or Clause 5, wherein the second input signal is derived from a criterion that includes a distance between the first robotic arm and the second robotic arm being less than a first distance threshold.

Clause 7. The medical system of any of Clauses 4-6, wherein the second input signal is derived from a criterion that includes a collision between a first surgical instrument coupled to the first robotic arm and a second surgical instrument coupled to the second robotic arm.

Clause 8. The medical system of any of Clauses 4-7, wherein the second input signal is derived from a criterion that includes a distance between a first surgical instrument coupled to the first robotic arm and a second surgical instrument coupled to the second robotic arm being less than a second distance threshold.

Clause 9. The medical system of any of Clauses 4-8, wherein the second input signal is derived from a criterion that includes a detection of a fault in the medical system.

Clause 10. The medical system of any of Clauses 4-9, wherein the second input signal is derived from a criterion that includes a detection of the first haptic interface device at a predefined boundary.

Clause 11. The medical system of any of Clauses 1-10, further comprising a second haptic interface device that is distinct and separate from the first haptic interface device.

Clause 12. The medical system of Clause 11, wherein the second input signal is derived from a criterion that includes a collision between the first haptic interface device and the second haptic interface device.

Clause 13. The medical system of Clause 11 or Clause 12, wherein the second input signal is derived from a criterion that includes a distance between the first haptic interface device and the second haptic interface device being less than a third distance threshold.

Clause 14. The medical system of any of Clauses 1-13, wherein the kinesthetic haptic feedback includes a continuous force applied against a user input.

Clause 15. The medical system of any of Clauses 1-14, wherein:

the second input signal is derived from a criterion that includes a plurality of events; and a distinct haptic feedback signal is selected as the vibrational tactile feedback signal for a respective event of the plurality of events.

Clause 16. The medical system of Clause 15, wherein the vibrational tactile feedback includes a component with a frequency of at least 10 Hz.

Clause 17. The medical system of any of Clauses 1-16, wherein the first haptic interface device further includes a motor to provide a torque about a roll axis of the first haptic interface device in response to a user input on the first haptic interface device.

Clause 18. A method, comprising:

receiving a first input signal from one or more input sensors;

sending to a first haptic interface device a kinesthetic haptic feedback signal based at least on the first input signal for a kinesthetic haptic feedback;

receiving a second input signal from the one or more input sensors; and sending to the first haptic interface device a vibrational tactile feedback signal based at least on the second input signal for a vibrational tactile feedback.

Clause 19. The method of Clause 18, wherein the first input signal is for controlling movement of a first robotic arm.

Clause 20. The method of Clause 19, wherein the first input signal is based on a difference between a master command and a movement of the first robotic arm.

Clause 21. The method of Clause 19 or Clause 20, wherein the second input signal is for controlling movement of a second robotic arm that is distinct from the first robotic arm.

Clause 22. The method of Clause 21, wherein the second input signal is derived from a collision between the first robotic arm and the second robotic arm.

Clause 23. The method of Clause 21 or Clause 22, wherein the second input signal is derived from a criterion that includes a distance between the first robotic arm and the second robotic arm being less than a first distance threshold.

Clause 24. The method of any of Clauses 21-23, wherein the second input signal is derived from a criterion that includes a collision between a first surgical instrument coupled to the first robotic arm and a second surgical instrument coupled to the second robotic arm.

Clause 25. The method of any of Clause 21-24, wherein the second input signal is derived from a criterion that includes a distance between a first surgical instrument coupled to the first robotic arm and a second surgical instrument coupled to the second robotic arm being less than a second distance threshold.

Clause 26. The method of any of Clauses 21-25, wherein the second input signal is derived from a criterion that includes a detection of a fault in a medical system.

Clause 27. The method of any of Clauses 21-26, wherein the second input signal is derived from a criterion that includes a detection of the first haptic interface device at a predefined boundary.

Clause 28. The method of any of Clauses 18-27, further comprising determining a position of a second haptic interface device that is distinct and separate from the first haptic interface device.

Clause 29. The method of Clause 28, wherein the second input signal is derived from a criterion that includes a collision between the first haptic interface device and the second haptic interface device.

Clause 30. The method of Clause 28 or Clause 29, wherein the second input signal is derived from a criterion that includes a distance between the first haptic interface device and the second haptic interface device being less than a third distance threshold.

Clause 31. The method of any of Clauses 18-30, wherein the kinesthetic haptic feedback includes a continuous force applied against a user input.

Clause 32. The method of any of Clauses 18-31, wherein:

the second input signal is derived from a criterion that includes a plurality of events; and a distinct haptic feedback signal is selected as the vibrational tactile feedback signal for a respective event of the plurality of events.

Clause 33. The method of Clause 32, wherein the vibrational tactile feedback includes a component with a frequency of at least 10 Hz.

Clause 34. The method of any of Clauses 18-33, wherein the first haptic interface device further includes a motor to provide a torque about a roll axis of the first haptic interface device in response to a user input on the first haptic interface device.

What is claimed is:

1. A medical system, comprising:

a first haptic interface device;

one or more input sensors;

one or more processors; and memory storing instructions, which, when executed by the one or more processors, cause the one or more processors to:

receive a first input signal from the one or more input sensors;

generate a kinesthetic haptic feedback signal based at least on the first input signal for a kinesthetic haptic feedback;

receive a second input signal from the one or more input sensors;

generate a vibrational tactile feedback signal based at least on the second input signal for a vibrational tactile feedback;

generate a control signal based on a combination of the kinesthetic haptic feedback signal and the vibrational tactile feedback signal; and send to the first haptic interface device the control signal.

2. The medical system of claim 1, further comprising a first robotic arm.

3. The medical system of claim 2, wherein the first input signal is based on a difference between a master command and a movement of the first robotic arm.

4. The medical system of claim 2, further comprising a second robotic arm that is distinct from the first robotic arm.

5. The medical system of claim 4, wherein the second input signal is derived from a collision between the first robotic arm and the second robotic arm.

6. The medical system of claim 4, wherein the second input signal is derived from a criterion that includes a distance between the first robotic arm and the second robotic arm being less than a distance threshold.

7. The medical system of claim 4, wherein the second input signal is derived from a criterion that includes a collision between a first surgical instrument coupled to the first robotic arm and a second surgical instrument coupled to the second robotic arm.

8. The medical system of claim 4, wherein the second input signal is derived from a criterion that includes a distance between a first surgical instrument coupled to the first robotic arm and a second surgical instrument coupled to the second robotic arm being less than a distance threshold.

9. The medical system of claim 4, wherein the second input signal is derived from a criterion that includes a detection of a fault in the medical system.

10. The medical system of claim 4, wherein the second input signal is derived from a criterion that includes a detection of the first haptic interface device at a predefined boundary.

11. The medical system of claim 1, further comprising a second haptic interface device that is distinct and separate from the first haptic interface device.

12. The medical system of claim 11, wherein the second input signal is derived from a criterion that includes a collision between the first haptic interface device and the second haptic interface device.

13. The medical system of claim 11, wherein the second input signal is derived from a criterion that includes a distance between the first haptic interface device and the second haptic interface device being less than a distance threshold.

14. The medical system of claim 1, wherein the kinesthetic haptic feedback includes a continuous force applied against a user input.

15. The medical system of claim 1, wherein:

the second input signal is derived from a criterion that includes a plurality of events; and a distinct haptic feedback signal is selected as the vibrational tactile feedback signal for a respective event of the plurality of events.

16. The medical system of claim 15, wherein the vibrational tactile feedback includes a component with a frequency of at least 10 Hz.

17. The medical system of claim 1, wherein the first haptic interface device further includes a motor to provide a torque about a roll axis of the first haptic interface device in response to a user input on the first haptic interface device.

18. A method, comprising:

receiving a first input signal from one or more input sensors;

generating a kinesthetic haptic feedback signal based at least on the first input signal for a kinesthetic haptic feedback;

receiving a second input signal from the one or more input sensors;

generating a vibrational tactile feedback signal based at least on the second input signal for a vibrational tactile feedback;

generating a control signal based on a combination of the kinesthetic haptic feedback signal and the vibrational tactile feedback signal; and sending to a first haptic interface device the control signal.

19. The method of claim 18, wherein the first input signal is for controlling movement of a first robotic arm, and wherein the second input signal is for controlling movement of a second robotic arm that is distinct from the first robotic arm.

20. The method of claim 19, wherein the first input signal is based on a difference between a master command and the movement of the first robotic arm, and wherein the second input signal is derived from a collision between the first robotic arm and the second robotic arm.

* * * * *